(12) United States Patent
San Antonio et al.

(10) Patent No.: US 11,154,638 B2
(45) Date of Patent: Oct. 26, 2021

(54) METHODS FOR FORMING SCAFFOLDS

(71) Applicant: Howmedica Osteonics Corp., Mahwah, NJ (US)

(72) Inventors: James Dominic San Antonio, Media, PA (US); Marc Gilles Long, Denville, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 15/234,239

(22) Filed: Aug. 11, 2016

(65) Prior Publication Data

US 2017/0043052 A1 Feb. 16, 2017

Related U.S. Application Data

(60) Provisional application No. 62/204,119, filed on Aug. 12, 2015.

(51) Int. Cl.
| | | |
|---|---|---|
| *A61L 27/18* | (2006.01) | |
| *A61L 27/54* | (2006.01) | |
| *A61L 27/56* | (2006.01) | |
| *A61L 27/46* | (2006.01) | |
| *A61L 27/12* | (2006.01) | |

(52) U.S. Cl.
CPC .............. *A61L 27/18* (2013.01); *A61L 27/12* (2013.01); *A61L 27/46* (2013.01); *A61L 27/54* (2013.01); *A61L 27/56* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 3,409,014 A | 11/1968 | Shannon | |
| 4,469,101 A | 9/1984 | Coleman et al. | |
| 4,655,777 A | 4/1987 | Dunn et al. | |
| 4,979,956 A | 12/1990 | Silvestrini | |
| 4,987,665 A | 1/1991 | Dumican et al. | |
| 5,711,960 A | 1/1998 | Shikinami | |
| 5,876,446 A | 3/1999 | Agrawal et al. | |
| 5,914,356 A | 6/1999 | Erbe | |
| 5,939,039 A | 8/1999 | Sapieszko et al. | |
| 5,989,463 A * | 11/1999 | Tracy ................... | A61K 9/1647 264/4.1 |
| 6,165,486 A | 12/2000 | Marra et al. | |
| 6,193,754 B1 | 2/2001 | Seedhom | |
| 6,379,962 B1 * | 4/2002 | Holy ....................... | A61L 27/18 435/395 |
| 6,383,519 B1 | 5/2002 | Sapieszko et al. | |
| 6,482,444 B1 | 11/2002 | Bellantone et al. | |
| 6,517,542 B1 | 2/2003 | Papay et al. | |
| 6,521,246 B2 | 2/2003 | Sapieszko et al. | |
| 6,599,323 B2 | 7/2003 | Melican et al. | |
| 6,709,744 B1 | 3/2004 | Day et al. | |
| 6,730,252 B1 | 5/2004 | Teoh et al. | |
| 6,756,060 B1 | 6/2004 | Greenspan et al. | |
| 6,852,330 B2 | 2/2005 | Bowman et al. | |
| 6,884,428 B2 | 4/2005 | Binette et al. | |
| 6,974,862 B2 | 12/2005 | Ringeisen et al. | |
| 6,991,803 B2 | 1/2006 | Sapieszko et al. | |
| 7,056,409 B2 | 6/2006 | Dubrow | |
| 7,074,294 B2 | 7/2006 | Dubrow | |
| 7,074,894 B2 | 7/2006 | Walker et al. | |
| 7,166,133 B2 | 1/2007 | Evans et al. | |
| 7,189,263 B2 | 3/2007 | Erbe et al. | |
| 7,214,765 B2 | 5/2007 | Ringeisen et al. | |
| 7,235,290 B2 | 6/2007 | Vallittu et al. | |
| 7,241,316 B2 | 7/2007 | Evans et al. | |
| 7,344,617 B2 | 3/2008 | Dubrow | |
| 7,368,124 B2 | 5/2008 | Chun et al. | |
| 7,378,088 B2 | 5/2008 | Kanemaru et al. | |
| 7,494,950 B2 | 2/2009 | Armitage et al. | |
| 7,517,539 B1 | 4/2009 | Lee et al. | |
| 7,519,017 B2 | 4/2009 | Yi | |
| 7,531,004 B2 | 5/2009 | Bagga et al. | |
| 7,534,451 B2 | 5/2009 | Erbe et al. | |
| 7,608,098 B1 | 10/2009 | Stone et al. | |

(Continued)

FOREIGN PATENT DOCUMENTS

| | | |
|---|---|---|
| CN | 104288833 A | 1/2015 |
| DE | 1604649 * | 12/2005 |

(Continued)

OTHER PUBLICATIONS

Horning et al. (Journal of Materials Chemistry, 19, 3838-3840, 2009) Synthetic polymeric nanoparticles by nanoprecipitation.*
Extended European Search Report for Application No. EP17169126.4 dated Oct. 10, 2017.
Albanese et al., Platelet rich plasma (PRP) in dental and oral surgery: from the wound healing to bone regeneration, Immunity and Ageing , Jun. 2013, vol. 10, No. 1, pp. 1-10.
Adams et at., J. of Knee Surgery, Tissue Engineering for Meniscus Repair, vol. 18(1), 2005, pp. 25-30.
Amoczky et aL, J. of Bone and Joint Surgery, Meniscal Repair Using an Exogenous Fibrin Clot, vol. 70A(8), 1988, pp. 1200-1217.
Australian Examination Report for Application No. 2007284135 dated Nov. 1, 2013.

(Continued)

*Primary Examiner* — Tigabu Kassa
(74) *Attorney, Agent, or Firm* — Lerner, David, Littenberg, Krumholz & Mentlik, LLP

(57) ABSTRACT

A method of forming a scaffold is disclosed herein. In some embodiments, a method of forming a scaffold includes dissolving a polymer in a solvent to form a polymer solution; adding additive precipitating agent to the polymer solution; precipitating and expanding the polymer from the polymer solution to form a scaffold; and removing the solvent from the scaffold. In some embodiments, prior to adding the precipitating agent, the method further comprising adding at least one of calcium phosphate or a bioactive additive to the polymer solution to form a mixture including the polymer solution and the at least one of calcium phosphate or bioactive additive.

20 Claims, 16 Drawing Sheets

(56) References Cited

U.S. PATENT DOCUMENTS

| | | |
|---|---|---|
| 7,651,769 B2 | 1/2010 | Dubrow |
| 7,651,869 B2 | 1/2010 | Saaski et al. |
| 7,723,395 B2 | 5/2010 | Ringeisen et al. |
| 7,842,737 B2 | 11/2010 | Wang et al. |
| 7,887,598 B2 | 2/2011 | Evans et al. |
| 7,892,291 B2 | 2/2011 | Evans et al. |
| 7,910,690 B2 | 3/2011 | Ringeisen et al. |
| 7,955,381 B1 | 6/2011 | Wang et al. |
| 7,959,940 B2 | 6/2011 | Gale et al. |
| 7,964,206 B2 | 6/2011 | Suokas et al. |
| 7,972,616 B2 | 7/2011 | Dubrow et al. |
| 7,985,475 B2 | 7/2011 | Dubrow |
| 8,071,007 B1 | 12/2011 | Teoh et al. |
| 8,114,161 B2 | 2/2012 | Evans et al. |
| 8,119,705 B2 | 2/2012 | Wang et al. |
| 8,128,626 B2 | 3/2012 | Justin |
| 8,133,500 B2 | 3/2012 | Ringeisen et al. |
| 8,167,881 B2 | 5/2012 | Justin |
| 8,188,229 B2 | 5/2012 | Ringeisen et al. |
| 8,192,665 B2 | 6/2012 | Huang et al. |
| 8,197,837 B2 | 6/2012 | Jamiolkowski et al. |
| 8,202,318 B2 | 6/2012 | Willobee |
| 8,287,915 B2 | 10/2012 | Clineff et al. |
| 8,298,284 B2 | 10/2012 | Cassani |
| 8,309,114 B2 | 11/2012 | Gale et al. |
| 8,343,530 B2 | 1/2013 | Wang et al. |
| 8,377,356 B2 | 2/2013 | Huang et al. |
| 8,389,588 B2 | 3/2013 | Ringeisen et al. |
| 8,394,139 B2 | 3/2013 | Roeder et al. |
| 8,394,488 B2 | 3/2013 | Dave et al. |
| 8,425,591 B1 | 4/2013 | Wang et al. |
| 8,425,619 B2 | 4/2013 | Evans et al. |
| 8,439,947 B2 | 5/2013 | Howard et al. |
| 8,445,554 B2 | 5/2013 | Ringeisen et al. |
| 8,475,531 B1 | 7/2013 | Maxson et al. |
| 8,512,735 B2 | 8/2013 | Gale et al. |
| 8,563,024 B2 | 10/2013 | Bratt et al. |
| 8,591,578 B2 | 11/2013 | Albertorio et al. |
| 8,613,877 B2 | 12/2013 | Huang et al. |
| 8,633,299 B2 | 1/2014 | Ringeisen et al. |
| 802,808 A1 | 4/2014 | Teoh et al. |
| 8,691,259 B2 | 4/2014 | Bowman et al. |
| 8,696,739 B2 | 4/2014 | Dierking et al. |
| 8,753,391 B2 | 6/2014 | Lu et al. |
| 8,778,378 B2 | 7/2014 | Clineff et al. |
| 8,821,494 B2 | 9/2014 | Pilgeram |
| 8,828,419 B2 | 9/2014 | Dave et al. |
| 8,834,468 B2 | 9/2014 | Justin |
| 8,858,617 B2 | 10/2014 | Roeder et al. |
| 8,864,843 B2 | 10/2014 | Lu et al. |
| 8,870,945 B2 | 10/2014 | Dave et al. |
| 8,876,864 B2 | 11/2014 | Spedden et al. |
| 8,895,045 B2 | 11/2014 | Jamiolkowski et al. |
| 8,956,637 B2 | 2/2015 | Dubrow et al. |
| 8,999,369 B2 | 4/2015 | Gale et al. |
| 9,144,482 B2 | 9/2015 | Sayet |
| 9,144,487 B2 | 9/2015 | Wang et al. |
| 9,199,004 B2 | 12/2015 | Wang et al. |
| 9,204,960 B2 | 12/2015 | Albertorio et al. |
| 9,211,184 B2 | 12/2015 | Stone et al. |
| 9,216,076 B2 | 12/2015 | Mitra et al. |
| 9,220,598 B2 | 12/2015 | Betz et al. |
| 9,226,815 B2 | 1/2016 | Schmieding et al. |
| 9,333,082 B2 | 5/2016 | Wei et al. |
| 9,445,803 B2 | 9/2016 | Marchand et al. |
| 9,504,557 B1 | 11/2016 | Samaniego et al. |
| 9,636,109 B2 | 5/2017 | Murphy et al. |
| 9,642,610 B2 | 5/2017 | Albertorio et al. |
| 9,801,707 B2 | 10/2017 | Cassani |
| 9,913,710 B2 | 3/2018 | Perriello et al. |
| 9,974,534 B2 | 5/2018 | Troxel et al. |
| 10,271,964 B1 | 4/2019 | Samaniego et al. |
| 10,357,355 B2 | 7/2019 | Woodruff et al. |
| 10,420,857 B2 | 9/2019 | Ringeisen et al. |
| 10,857,261 B2 | 12/2020 | D'Agostino et al. |
| 2002/0055759 A1 | 5/2002 | Shibuya |
| 2002/0127265 A1 | 9/2002 | Bowman et al. |
| 2002/0165611 A1 | 11/2002 | Enzerink et al. |
| 2002/0183858 A1 | 12/2002 | Contiliano et al. |
| 2003/0003127 A1 | 1/2003 | Brown et al. |
| 2004/0062753 A1 | 4/2004 | Rezania et al. |
| 2004/0078090 A1 | 4/2004 | Binette et al. |
| 2004/0185085 A1 | 9/2004 | Ochi et al. |
| 2004/0197367 A1 | 10/2004 | Rezania et al. |
| 2004/0197375 A1 | 10/2004 | Rezania et al. |
| 2005/0031704 A1* | 2/2005 | Ahn ............... C01B 25/32 424/602 |
| 2005/0161857 A1 | 7/2005 | Coombes et al. |
| 2005/0208094 A1 | 9/2005 | Armitage et al. |
| 2006/0178748 A1 | 8/2006 | Dinger et al. |
| 2006/0195179 A1 | 8/2006 | Sun et al. |
| 2006/0233887 A1 | 10/2006 | Day |
| 2007/0093912 A1 | 4/2007 | Borden |
| 2007/0218424 A1 | 9/2007 | Vuorisalo et al. |
| 2007/0255422 A1 | 11/2007 | Wei et al. |
| 2008/0051881 A1 | 2/2008 | Feng et al. |
| 2008/0081063 A1 | 4/2008 | Wang et al. |
| 2008/0082177 A1 | 4/2008 | Yang et al. |
| 2008/0085292 A1 | 4/2008 | Rezania et al. |
| 2009/0028921 A1* | 1/2009 | Arinzeh ............ A61F 2/28 424/423 |
| 2009/0075382 A1 | 3/2009 | Sachlos |
| 2009/0163936 A1 | 6/2009 | Yang et al. |
| 2009/0198167 A1 | 8/2009 | Ambrosio |
| 2009/0220566 A1 | 9/2009 | Barralet et al. |
| 2009/0312792 A1 | 12/2009 | Fallin et al. |
| 2009/0318962 A1 | 12/2009 | Spedden et al. |
| 2010/0047309 A1 | 2/2010 | Lu et al. |
| 2010/0113642 A1 | 5/2010 | Leskela et al. |
| 2010/0234947 A1 | 9/2010 | Ben Rubi et al. |
| 2010/0234966 A1 | 9/2010 | Lo |
| 2010/0310623 A1 | 12/2010 | Laurencin et al. |
| 2011/0022085 A1 | 1/2011 | Murphy et al. |
| 2011/0097801 A1 | 4/2011 | Miller |
| 2011/0098727 A1 | 4/2011 | Kaiser et al. |
| 2011/0118827 A1 | 5/2011 | Wu |
| 2011/0125189 A1 | 5/2011 | Stoll, Jr. et al. |
| 2012/0029561 A1 | 2/2012 | Olson |
| 2012/0040015 A1 | 2/2012 | Lehtonen et al. |
| 2012/0071566 A1 | 3/2012 | Kelly et al. |
| 2012/0101593 A1 | 4/2012 | D'Agostino et al. |
| 2013/0059011 A1* | 3/2013 | Clineff ............ A61L 27/58 424/602 |
| 2013/0090686 A1 | 4/2013 | Stopek et al. |
| 2013/0131722 A1 | 5/2013 | Marchand et al. |
| 2013/0202670 A1 | 8/2013 | Darmoc et al. |
| 2013/0238027 A1 | 9/2013 | Zhang et al. |
| 2013/0282140 A1 | 10/2013 | Ringeisen et al. |
| 2014/0039552 A1 | 2/2014 | Pilgeram |
| 2014/0142686 A1 | 5/2014 | Wu |
| 2014/0186441 A1 | 7/2014 | Beck et al. |
| 2014/0200667 A1 | 7/2014 | Carter |
| 2014/0207138 A1 | 7/2014 | Justin |
| 2014/0287014 A1 | 9/2014 | Ringeisen et al. |
| 2014/0350680 A1 | 11/2014 | Le et al. |
| 2015/0018878 A1 | 1/2015 | Rizk et al. |
| 2015/0051643 A1 | 2/2015 | Spedden et al. |
| 2015/0100121 A1 | 4/2015 | Lu et al. |
| 2015/0230918 A1 | 8/2015 | Detamore et al. |
| 2016/0000974 A1 | 1/2016 | Arinzeh et al. |
| 2016/0144066 A1 | 5/2016 | Long et al. |
| 2017/0043052 A1 | 2/2017 | San Antonio et al. |
| 2020/0360573 A1 | 11/2020 | Davison et al. |

FOREIGN PATENT DOCUMENTS

| | | |
|---|---|---|
| JP | 2001523483 A | 11/2001 |
| WO | 01038428 A1 | 5/2001 |

(56) References Cited

FOREIGN PATENT DOCUMENTS

| WO | 0240069 A2 | 5/2002 | |
| WO | WO-2008134807 A1 * | 11/2008 | ............ C08J 9/0004 |

OTHER PUBLICATIONS

Australian Examination Report for Application No. 2007284135 dated Sep. 9, 2013.
European Search Report for Application No. EP07800009.8 dated Feb. 12, 2015.
Fox et al, J. of Arthroscopic and Related Surgery, Treytination of Incomplegte Meniscal Tears,9(4), 1993, pp. 451-455.
Gomez-Vega et al., "Bioactive Glass Coatings with Hydroxyapatite and Bioglass Particles on Ti-based Implants, 1. Processing," Biomaterials, Jan. 2000, pp. 105-111, vol. 21.
O'Meara, p., Orthopaedic Review, The Basic Science of Meniscus Repair, Jun. 1993, pp. 681-686.
Okuda et aL, J of Arthroscopic and Related Surgery, Meniscal Rasping for Repair of Meniscal Tear in the Avascular Zone, vol. 15(3),1999, pp. 281-286.
Sgaglione et at., J. of Arthroscopic and Related Surgery, Current Concpets in Meniscus Surgery Resection to Replacement, vol. 19(10), 2003, pp. 161-188.
Smith & Nephew Technique Plus Illustrated Guide—Meniscal Repair with the FasT-Fix Suture System.
Supplementary European Search Report dated Jul. 28, 2008 in connection with corresponding European Application No. EP 05 73 9944.
U.S. Appl. No. 10/983,236.
U.S. Appl. No. 10/984,624.
Zhang et at., Am. J. of Sports Medidne, Repairs by Trephination and Suturing of Longitudinal Injuries in the AvascularArea of the Meniscus in Goats, vol. 23(1), 1995, pp. 35-41.
Aparecida et al., "Biomimetic apatite formation on Ultra-High Molecular Weight Polyethylene (UHMWPE) using modified biomimetic solution", J. Mater Sci: Mater Med (200(0 20:1215-1222.
Stamboulis et al., "Mechanical properties of biodegradable polymer sutures coated with bioactive glass", Journal of Materials Science: MAterials in Medicine 13 (2002) 843-848.
Bretcanu et al., "Bioactivity of degradable polymer sutures coated with bioactive glass", Journal of Materials Science: Materials in Medicine 15 (2004) 893-899.
Boccaccini e al., "Composite surgical sutures with bioactive glass coating", Journal of Biomedical Materials REsearch Part B: Applied Biomaterials, vol. 67B, Issue 1, pp. 618-626, Oct. 15, 2003.
Bordes, C., et al., 2010, International J. Pharmaceutics, 383, 236-243.
K. Makomkaewkeyoon, Polycaprolactone Matrices generated in aqueous media: natural polymers immobilization and stress relaxation behavior. Masters thesis, Oklahoma State University, 2007, 74 pages.
B. Azimi, et al. Journal of Engineering Fibers and Fabrics vol. 9, Issue 3 (2014) p. 74-90.
M.A. Woodruff and D.W. Hutmacher, The return of a forgotten polymer: polycaprolactone in the 21st century, Progress in Polymer Science, p. 1-102, Elsevier Press, 2010.
S.W. Pok, et.al, In vitro characterization of polycaprolactone matrices generated in aqueous media, Acta Biomater. Mar. 2010 ; 6(3): 1061-1068.
A. Oryan et al., Bone regenerative medicine: classic options, novel strategies, and future directions, J. Orthop. Surg. Res. Mar. 17, 2014; 9(1):18.
A.G.A. Coombes et al, Precipitation Casting of Polycaprolactone for Applications in Tissue Engineering and Drug Delivery, Biomaterials 2004, 25, 315-325.
W.D. Kingery, Introduction to Ceramics, Wiley Series on the Science and Technology of Materials, 1st Ed, Hollowman, J.H., et al. (EDs.), Wiley & Sons, 1960, p. 409-417.
Gosain, A. Bioactive Glass for Bone Replacement in Craniomaxillofacial Reconstruction, Plastic and Reconstructive Surgery (2004) vol. 114, No. 2, pp. 590-593.
European Search Report for Application No. 16183881.8 dated Dec. 19, 2016.
Amoczky et aL, J. of Bone and Joint Surgery, Meniscal Repair Using an Exogenous Fibrin Clot, vol. 70A(8), Sep. 1988, pp. 1200-1217.
Australian Search Report for Application No. 2016213743 dated Feb. 21, 2020, 1 page.
European Search Report for Application No. EP 20185803.2, dated Jan. 21, 2021, 10 pages.
European Search Report for Application No. EP 20187075.5, dated Jan. 26, 2021, 8 pages.

* cited by examiner

METHODS FOR FORMING SCAFFOLDS

CROSS-REFERENCE TO RELATED APPLICATION

The present application claims priority to U.S. Application Ser. No. 62/204,119, filed Aug. 12, 2015, which is incorporated herein by reference.

BACKGROUND OF THE INVENTION

Bone graft materials are used in many applications within the orthopedic and/or other medical fields, such as to cause fusion of adjacent bone parts to repair a fracture, to fuse a joint(s) and alleviate pain at the joint(s), and/or more securely attach an implant or other device to bone. Bone graft materials have numerous indications within the orthopedic field, which rely on the ability of the material to facilitate natural bone growth at the repair site (e.g., for regenerating and/or forming additional bone at the site).

There has been a continuing need for improved bone graft materials. For example, autograft devices, which are processed from a patient's own bone, have the ideal properties and radiopacity. However, the use of autogenous bone exposes the patient to a second surgery, pain, and morbidity at the donor site. Allograft devices, which are processed from donor bone, also carry the risk of disease transmission. These devices are restricted in terms of variations on shape and size and have sub-optimal strength properties that decrease after implantation. The quality of the allograft devices varies because the devices are natural. Also, since companies that provide allograft implants obtain their supply from donor tissue banks, there tend to be limitations on supply.

In recent years, synthetic materials have become a viable alternative to autograft and allograft devices. Most synthetic materials share numerous advantages over allografts, autografts and demineralized bone matrix ("DBM"), such as unlimited supply, elimination of disease transmission, elimination of second surgery, and the ability to be shaped into various shapes and sizes. Many synthetic bone grafts include materials that closely mimic mammalian bone, such as compositions containing calcium phosphates. Exemplary calcium phosphate compositions contain type-B carbonated hydroxyapatite $[Ca_5(PO_4)_{3x}(CO_3)x(OH)]$, which is the principal mineral phase found in the mammalian body. Calcium phosphate ceramics have been fabricated and implanted in mammals in various forms including, but not limited to, shaped bodies and cements. Different stoichiometric compositions such as hydroxyapatite ("HAp"), tricalcium phosphate ("TCP"), tetracalcium phosphate ("TTCP"), and other calcium phosphate salts and minerals, have all been employed to match the adaptability, biocompatibility, structure, and strength of natural bone. The role of pore size and porosity profile in promoting revascularization, healing, and remodeling of bone have been recognized as a critical property for bone grafting materials. The preparation of exemplary porous calcium phosphate materials that closely resemble bone have been disclosed, for instance, in U.S. Pat. Nos. 6,383,519; 6,521,246 and 6,991,803, which are incorporated herein by reference in their entirety.

The Vitoss® line of synthetic bone graft products (manufactured by Stryker Orthobiologics, Malvern, Pa.) includes β-TCP (i.e., beta tri-calcium phosphate), collagen, and/or bioactive glass.

Scaffolds may be used to support bone graft materials. Among the most commonly used scaffolds in medical devices are mammalian-derived collagens (A. Oyran et al., J. Orthop. Surg. Res. 2014 Mar. 17; 9(1):18).

Synthetic scaffolds using biocompatible polymers, such as PCL are also available and may be formed by, or using, molding, solvent casting, particulate leaching, solvent evaporation, electrospun fibers or meshes thereof, and 3-D printed constructs. (see M. A. Woodruff and D. W. Hutmacher, The return of a forgotten polymer: Polycaprolactone in the $21^{st}$ century. Progress in Polymer Science, p. 1-102, Elsevier Press (2010)) Highly ordered, crystalline constructs having properties akin to those of solvent casted scaffolds can also be formed. (A. G. A. Coombes et al., Biomaterials 25 (2004) 315-325). Unfortunately, those synthetic scaffolds lack the foam-like consistency, and are of a higher density and stiffer, and lack several desirable properties, such as porosity to soak up and retain biological fluids, moldability and compressibility to fit into a hole or defect in bone.

Despite advances in synthetic materials for bone graft applications, there remains a need in the art for further improvements, such as materials having tunable properties, lacking animal tissue-derived materials, and which can be manufactured without complex methods.

BRIEF SUMMARY OF THE INVENTION

Scaffolds and methods of forming the same are disclosed herein. In some embodiments, a method of forming a scaffold includes dissolving a polymer in a solvent to form a polymer solution; adding a precipitating agent to the polymer solution; precipitating and expanding the polymer from the polymer solution to form a scaffold; and removing the solvent from the scaffold.

In some embodiments, a method of forming a scaffold includes dissolving a polymer in a solvent to form a polymer solution; adding a precipitating agent to the polymer solution; precipitating the polymer from the polymer solution to form a scaffold comprising an amorphous polymer matrix; and removing the solvent from the scaffold.

In some embodiments, a method of forming a scaffold includes dissolving a polymer in a solvent to form a polymer solution; adding a precipitating agent to the polymer solution; precipitating the polymer from the polymer solution to form a scaffold, wherein the time to form the scaffold by precipitation of the polymer ranges from about 1 minutes to about 1 hour; and removing the solvent from the scaffold.

In some embodiments, a method of forming a scaffold includes dissolving a polymer in a solvent to form a polymer solution; adding a precipitating agent to the polymer solution; precipitating the polymer from the polymer solution to form a scaffold, wherein a weight ratio of the precipitating agent to the polymer solution ranges from about 0.05:1 to about 3.5:1; and removing the solvent from the scaffold.

In some embodiments, a scaffold comprises an amorphous polymer matrix having a density ranging from about 0.025 $g/cm^3$ to about 0.063 $g/cm^3$.

In some embodiments, a scaffold comprises an amorphous polymer matrix having at least one of calcium phosphate or bioactive material embedded therein.

In some embodiments, prior to adding the precipitating agent, the method further comprises adding at least one of calcium phosphate or a bioactive additive to the polymer solution to form a mixture, wherein after precipitating the polymer, the scaffold formed includes the at least one of calcium phosphate or bioactive additive embedded therein.

In some embodiments, an amount of calcium phosphate ranges from about 15 weight % to about 40 weight %, based on the total weight of the mixture.

In some embodiments, the method further comprises, prior to adding the at least one of calcium phosphate or bioactive additive to the polymer solution, soaking the at least one of calcium phosphate or bioactive material with the precipitating agent to form a precipitating agent-soaked additive; and freezing the precipitating agent-soaked additive.

In some embodiments, the method further comprises, prior to precipitating the polymer, freezing the mixture.

In some embodiments, the precipitating agent is selected from the group consisting of water, ethanol, 1-propanol, isopropyl ether, 2-butanol, hexane, and mixtures thereof.

In some embodiments, the method further comprises adding the precipitating agent drop wise.

In some embodiments, the method further comprises adding the precipitating agent by spraying or misting the precipitating agent onto a surface of the polymer solution or the mixture of polymer solution and at least one of calcium phosphate or bioactive additive.

In some embodiments, the method further comprises adding the precipitating agent by flowing or pouring the precipitation agent onto the surface of the polymer solution or the mixture of polymer solution and at least one of calcium phosphate or bioactive additive.

In some embodiments, the polymer solution or the mixture of polymer solution and at least one of calcium phosphate or bioactive additive is submerged in the precipitating agent.

In some embodiments, the method further comprises, prior to precipitating the polymer, placing the mixture into a mold.

In some embodiments, the method further comprises, prior to precipitating the polymer, depositing the mixture on a substrate.

In some embodiments, the substrate is selected from the group consisting of a mesh or screen, a porous polymer substrate, a bone suture anchor, a porous metal implant, living tissue, decellularized tissue, and mixtures thereof.

In some embodiments, prior to precipitating the polymer, the method further comprises soaking the substrate with the precipitating agent.

In some embodiments, the polymer is at least one selected from the group consisting of polycaprolactones (PCL), polyglycolides (PGA), polylactic acids (PLA), polyethylene, polypropylene, polystyrene, poly(D,L-lactic-co-glycolide) (PLGA), polyglycolic acid (PGA), poly-L-Lactic acid (PL-LA), polysulfones, polyolefins, polyvinyl alcohol (PVA), polyalkenoics, polyacrylic acids (PAA), polyesters, lower alkyl cellulose ethers, methylcellulose, sodium carboxymethyl cellulose, hydroxyethyl cellulose, hydroxypropyl cellulose, hydroxypropylmethylcellulose, carboxymethyl cellulose, and mixtures thereof.

In some embodiments, the calcium phosphate is at least one selected from the group consisting of tetra-calcium phosphate, di-calcium phosphate, dicalcium phosphate dihydrous, dicalcium phosphate anhydrous, tri-calcium phosphate, mono-calcium phosphate, β-tricalcium phosphate, α-tricalcium phosphate, oxypatite, hydroxypatite, and mixtures thereof.

In some embodiments, the calcium phosphate is porous.

In some embodiments, the solvent is at least one selected from the group consisting of glacial acetic acid (GAA), acetic acid, anisole, chloroform, methylene chloride, acetylchloride, 2,2,2 trifluoroethanol, trifluoroacetic acid, 1,2-Dochloroethane, and mixtures thereof.

In some embodiments, the bioactive additive is at least one selected from the group consisting of bioactive glass, bone chips, demineralized bone chips or powder, living cells, lyophilized bone marrow, collagen, other bioactive proteins or growth factors, biologics, peptides, glycosaminoglycans, anti-inflammatory compounds, antibiotics, antimicrobial elements, and mixtures thereof.

In some embodiments, the polymer is polycaprolactone (PCL) and wherein the solvent is glacial acetic acid (GAA).

In some embodiments, the polymer is polycaprolactone (PCL) and wherein the solvent is anisole.

In some embodiments, an amount of polymer dissolved in the polymer solution ranges from about 4 wt % to about 15 wt %, relative to the total weight of the polymer solution.

In some embodiments, the calcium phosphate is β-tricalcium phosphate (β-TCP).

In some embodiments, an amount of calcium phosphate ranges from about 20 wt % to about 30 wt %, relative to the total weight of the mixture.

In some embodiments, the polymer has a molecular weight ranging from about 3,000 g/mol to about 150,000 g/mol.

In some embodiments, the time to form the scaffold by precipitation of the polymer ranges from about 1 minute to about 1 hour.

In some embodiments, the time to form the scaffold by precipitation ranges from about 5 minutes to about 30 minutes.

In some embodiments, a weight ratio of the precipitating agent to the polymer solution ranges from about 0.05:1 to about 3.5:1.

In some embodiments, a weight ratio of the precipitating agent to the polymer solution ranges from about 0.5:1 to about 3:1.

In some embodiments, an amount of calcium phosphate ranges from about 15 weight % to about 40 weight %, based on the total weight of the mixture.

In some embodiments, removal of the solvent further includes removal of the precipitating agent.

In some embodiments, a time for removal of the solvent and/or the precipitating agent ranges from about 5 minutes to about 3 hours.

In some embodiments, a time for removal of the solvent and/or the precipitating agent ranges from about 5 minutes to about 1 hour.

In some embodiments, a time for removal of the solvent and/or the precipitating agent ranges from about 5 minutes to about 30 minutes.

In some embodiments, a time for removal of the solvent and/or the precipitating agent ranges from about 20 minutes to about 30 minutes.

In some embodiments, the scaffold comprises an amorphous polymer matrix.

In some embodiments, the scaffold comprises at least one of calcium phosphate or a bioactive additive embedded in the amorphous polymer matrix.

DETAILED DESCRIPTION

Figure 1A:
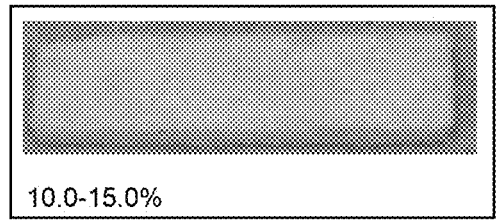
FIGS. 1A-D depict scaffolds made using a range of concentrations for a polymer solution in accordance with some embodiments of the present invention.

The present invention will be described in more detail below.

All percentages and ratios used herein are by weight of the total composition and all measurements made are at about room temperature and normal pressure unless otherwise designated. "Room temperature" as defined herein means a temperature ranging between about 22° C. and about 26° C. All temperatures are in degrees Celsius unless specified otherwise.

The present invention can comprise (open ended) or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise.

As used herein, "consisting essentially of" means that the invention may include ingredients in addition to those recited in the claim, but only if the additional ingredients do not materially alter the basic and novel characteristics of the claimed invention. Preferably, such additional ingredients will not be present at all or only in trace amounts. However, it may be possible to include up to about 10% by weight of materials that could materially alter the basic and novel characteristics of the invention as long as the utility of the compounds (as opposed to the degree of utility) is maintained.

All ranges recited herein may include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

It should be further understood that a description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.3, 3, 4, 5, 5.7 and 6. This applies regardless of the breadth of the range.

The terms such as "at least one of calcium phosphate or bioactive additive", "calcium phosphate and/or bioactive additive", and "bioactive additive and/or calcium phosphate" are used interchangeably through the specification and should be understood to mean "calcium phosphate without bioactive additive, bioactive additive without calcium phosphate, or both calcium phosphate and bioactive additive."

The terms "weight percent of the polymer solution" or "polymer concentration" and "weight percent of the mixture" as used herein have different meanings. The terms "weight percent of the polymer solution" or "polymer concentration" are defined as the weight of the polymer relative to the weight of the solvent. For example, a 10 wt % PCL-GAA solution may have 10 grams of PCL relative to 100 grams of GAA. In contrast, the term "weight percent of the mixture" is defined as the weight of a component of the mixture relative to the total weight of the mixture including the component. For example, a mixture of calcium phosphate and 10 wt % PCL-GAA solution having an amount of 10 wt % calcium phosphate may be 10 grams of calcium phosphate to 100 grams of the total weight of the mixture, i.e., the summed weight of calcium phosphate and 10 wt % PCL-GAA solution. The term "weight ratio" as used herein is defined as the weight of one component to the weight of another component. For example, a weight ratio of 6 grams of water to 2 grams of a 10% PCL-GAA solutions is 6:2.

The term 'molecular weight' as used herein in regards to a molecular weight of a polymer is a weight average molecular weight ($M_w$) unless otherwise specified. If a number average molecular weight of a polymer is used, it is indicated as $M_n$.

The terms 'foam', 'foam-like', 'foaming' as used herein are not intended to describe a scaffold comprising a classically defined foam or formed by foaming, where a classically defined foam comprises a mass of small bubbles in a liquid. The terms 'foam', 'foam-like', or 'foaming' as used herein describe a physical appearance of a scaffold as similar to that of Styrofoam or seam-foam.

The terms "expansion", or "expanding" as used herein to describe an increase in a volume or space that a group of polymer molecules occupy upon or while precipitating from a polymer solution or an increase in the volume of the scaffold formed upon precipitation. A scaffold formed from a precipitated and expanded polymer initially present in a polymer solution, or a precipitated and expanded polymer initially present in a mixture including the polymer solution and at least one of calcium phosphate or a bioactive additive, can have a structure that is foam-like and/or amorphous.

Methods

Described herein are methods of making a scaffold in accordance with some embodiments of the present invention. In one embodiment, a method of preparing a scaffold may include dissolving a polymer in a solvent to form a polymer solution; adding a precipitating agent to the polymer solution; precipitating and expanding the polymer from the polymer solution to form the scaffold; and removing the solvent from the scaffold.

The method described herein can employ a two phase system to form a scaffold. The two phase system may comprise a polymer solution as one phase and precipitating agent as the other phase. Chemical reactivity resulting from the precipitating agent being introduced into the polymer solution induces rapid intermixing, precipitation and expansion of the polymer to form the scaffold. Scaffolds can be formed within minutes and can be relatively homogeneous, amorphous, non-crystalline, foam-like, and porous, having irregularly-sized holes and channels. The method does not use a foaming agent to achieve a scaffold having a foam-like structure. In one embodiment, the polymer solution can be a viscous solution, such as PCL dissolved in glacial acetic acid. In one embodiment, the precipitating agent can be water, a non-organic low viscosity solvent.

The polymer may include one or more polymers as discussed herein. A solvent may include any suitable solvent that is capable of dissolving the polymer, and may vary depending on the polymer that is being dissolved. Exemplary solvents may include, without limitation, one or more of glacial acetic acid (GAA), anisole, chloroform, methylene chloride, acetylchloride, 2,2,2 trifluoroethanol, trifluoroacetic acid, and/or 1,2-Dochloroethane. Other solvents that may be utilized with the inventive methods may be found in Bordes, C., et al., 2010, International J. Pharmaceutics, 383, 236-243, which is incorporated herein by reference.

The polymer can be dissolved in the solvent in any suitable concentration necessary to produce a scaffold having the desired properties. The concentration of polymer in the polymer solution may influence mechanical properties of the resulting scaffold, such as flexibility and ability to retain calcium phosphate or bioactive additive. In some embodiments, physical and chemical properties of the polymer solution, such as molecular weight, specific gravity, polarity, or the like, may have an influence on the morphology of the scaffold formed therefrom. In some embodiments, morphology of the scaffold may be modified, at least partially, by identity of polymer and/or solvent.

The concentration of polymer in solution may depend on the polymer and solvent used. For example, the solubility of PCL in many different solvents was reported in Bordes, C., et al., where it is noted that depending on the solvent used, PCL having a range of molecular weights may be soluble at up to 50 wt % solutions. In some embodiments, the polymer concentration may range from about 1 wt % to about 50 wt %, relative to the weight of solvent, preferably from about 5.0 wt % to about 15 wt %, more preferably from about 7.0 wt % to about 10 wt % of the polymer solution. The polymer concentration range may be above 50 wt % in some embodiments. In some embodiments, the polymer may be present in a saturated amount or supersaturated amount in the polymer solution. In some embodiments, the polymer may be PCL and the solvent may be GAA, where PCL is dissolved in GAA ranging from about 7.0 wt % to greater than about 10 wt %, or to a saturated level. In some embodiments, the saturated level may be in excess of about 10 wt % but less that about 15 wt % for PCL dissolved in GAA. As shown in FIG. 1, PCL solutions ranging from about 7.0 wt % to up to a saturated level (labeled as 10%-15%) can produce scaffolds that retain a shape of a mold in which they were made, and retain calcium phosphate, which is embedded in the scaffold during the molding process. In some embodiments, higher concentrations of PCL in solution may be achieved using anisole as a solvent, instead of GAA. In such an embodiment, PCL may be dissolved in anisole from about 10 wt % to about 50 wt %. For example, PCL having a molecular weight of about 14,000 g/mol was soluble in anisole at up to 50% wt %, and PCL having a molecular weight of 65,000 g/mol may be dissolved at 10 wt % but less than 50 wt %.

The method may include precipitating the polymer from the polymer solution to form the scaffold. Alternatively, when calcium phosphate and/or bioactive additive is used (described further below), the polymer may be precipitated from a mixture formed from calcium phosphate and/or bioactive additive added to the polymer solution. The precipitation of the polymer from the polymer solution may generate a scaffold that is fluffy, amorphous, absorbent, and low density, unlike higher density scaffolds generated using other methods. A low density scaffold may be more porous, deformable, drapable, compressible, not load bearing to a significant extent, and able to tear apart by hand, in contrast to a high density scaffold. A high density scaffold would be less porous, somewhat load bearing, rigid and marginally, if at all drapable, not very compressible, and difficult, if not impossible to tear apart by hand, compared with a low density scaffold. In some embodiments, scaffolds of medium or high density can also be achieved using methods discussed herein. In some embodiments, the scaffolds can resist hand pressure to some extent as well as retaining fluid even when a force ten or more times its weight is applied. In some embodiments, compression resistance of the scaffold may depend on any or all of polymer concentration in the polymer solution, polymer molecular weight, and amount of calcium phosphate and/or bioactive additive used.

The polymer may be precipitated by contacting the polymer solution or the mixture with a precipitating agent to form the scaffold. In some embodiments, the entire scaffold can be formed by contacting the polymer solution or mixture with the precipitating agent. For example, the scaffold is not formed piecewise by using a precipitating agent to precipitate a portion of the polymer, and removing solvent to precipitate another portion of the polymer. In some embodiments, a scaffold having a foam-like and/or amorphous structure is not formed in the absence of a precipitating agent. For example, removal of solvent to precipitate the polymer in the absence of a precipitating agent does not form a scaffold having a foam-like and/or amorphous structure. Exemplary precipitating agents can include, without limitation, water, ethanol, 1-propanol, isopropyl ether, 2-butanol, hexane, or combinations thereof. The total time to precipitate a scaffold can be on the order of minutes. In some embodiments, a precipitation time may range from about 1 minute to about 30 minutes. In other embodiments, the precipitation time may range from about 5 minutes to 25 minutes. In yet other embodiments, the precipitation time may range from 10 minutes to 20 minutes. In yet other embodiments, a precipitation time up to 1 hour may be utilized.

The polymer may be precipitated in various ways. For example, in some embodiments where a mold is used, the precipitating agent may be initially added drop wise to an exposed surface of the polymer solution disposed in the mold. The mold may, optionally, then be submerged in the precipitating agent. In some embodiments, when the polymer solution is present on a substrate, the polymer solution including the substrate may be immersed in the precipitating agent to precipitate the polymer to form the scaffold. In some embodiments, the precipitating agent may be sprayed or misted onto a surface of the polymer solution or a mixture including the polymer solution and at least one of calcium phosphate or bioactive additive. In some embodiments, the precipitating agent may be flowed or poured onto the surface of the polymer solution or the mixture of polymer solution and at least one of calcium phosphate or bioactive additive. The amount of precipitation agent added and/or its speed of addition may strongly influence the foam-like qualities and density of the resulting scaffold.

In some embodiments, an order in which method steps are performed may determine the morphology of a resulting scaffold. One exemplary embodiment is described in Experimental Example 6 below. Under some conditions, a scaffold formed by dropwise adding of a precipitating agent to a polymer solution may result in a fluffy, amorphous, foam-like scaffold. Under some conditions, when the same amount of polymer solution is dropwise added to a precipitating agent, the resulting scaffold can be irregularly shaped and has non-homogenous density.

The polymer can expand upon or while precipitating from the polymer solution or a mixture including the polymer solution and at least one of calcium phosphate or a bioactive active. In some embodiments, precipitation and expansion of the polymer occur simultaneously. In some embodiments, the amount of precipitating agent and/or the speed at which it is added may cause both precipitation and expansion of the scaffold. One exemplary embodiment is described in Experimental Example 6. When no precipitating agent is used, and the scaffold is precipitated through air drying, the scaffold is dense, slightly flexible when manipulated by hand, and appears to have little or no porosity based on visual inspection. As an amount of precipitating agent is increased relative to the amount of PCL solution, the resulting scaffold is less dense, porous, fluffy, and Styrofoam-like in appearance. If the amount of precipitating agent is increased too far relative to the amount of PCL solution, the scaffold continues to expand, but can expand into scaffolds of irregular shapes. In some embodiments, a weight ratio of precipitating agent to a polymer solution may range from about 0.05:1 to about 3.5:1. In some embodiments, the weight ratio may range from about 0.5:1 to 3:1. In yet other embodiments, the weight ratio may range in excess of 3.5:1.

The expansion of the scaffold can be controlled by an amount of precipitating agent added. The expansion can alter the density and/or porosity of the scaffold relative to a scaffold where no precipitating agent is used. In some embodiments, the scaffold has a thickness that may be at least about 2 times that of a scaffold where no precipitating agent is used. In some embodiments, the scaffold has a thickness that may be at least about 3 times up to about 8 times. In yet another embodiment, the scaffold has a thickness that may be at least about 1 order of magnitude greater than that of a scaffold where no precipitating agent is used. In yet another embodiment, the scaffold has a thickness that is greater than about 1 order of magnitude may be utilized.

In some embodiments, a density of the scaffold may have an inverse linear relationship with thickness of the expanded scaffold. For example, a scaffold made using a precipitating agent may have about 2 times the thickness of a scaffold made without the use of a precipitating agent, and about 50% of the density. In some embodiments, the density of a scaffold made using a precipitating agent may range from about 90% to about 14% of the density of a scaffold made without using a precipitating agent. In some embodiments, the density may range from about 70% to about 14%. In other embodiments, the density may range from about 50% to 14%. In yet other embodiments, the density may range from about 40% to about 14%. In yet other embodiments, the density may range from about 29% to about 14%. In yet another embodiment, the density may be less than 14%. In yet another embodiment, a density of about 11% or less may be utilized. However, the relationship may not necessarily be inverse linear in all cases, and may depend on the shape of the mold used to make the scaffold.

The porosity of a scaffold made with a precipitating agent may be greater than that of a scaffold made without a precipitating agent. In some embodiments, as density of the scaffold decreases, such as when an amount of precipitating agent added is increased, a fluid holding capacity, or porosity, can increase.

In some embodiments, surface topology of the scaffold and perhaps to some extent scaffold thickness may be controlled based on how the precipitating agent is added to the surface of the mixture. For example, a uniform, fine spray may yield a flat, dense surface. In other embodiments, a slow, drop wise pipetting can result in a dimpled, fluffy surface. Slow to sudden submersion to various depths below the surface of the precipitating agent may result in scaffolds having differing degrees of fluffy, sea foam-like surfaces and thicknesses. When precipitating agent addition is carefully controlled by drop wise addition or a fine water spray, the dimensions of the resulting scaffolds can roughly approximate that of the molds in which they are cast. In some embodiments, a mold may have a thickness ranging from about 5 mm to about 30 mm. In some embodiments, a mold has a thickness exceeding about 30 mm. In some embodiments, any suitable thickness of mold can be utilized. In some embodiments, depending on a method of scaffold precipitation the scaffold may exceed the thickness of the mold by one or more millimeters. The method may include adding at least one of calcium phosphate and/or bioactive additive to the polymer solution to form a mixture. Any suitable calcium phosphate or bioactive additive may be utilized. The mixture may vary from a solution, or suspension, or a paste, depending on the application. For example, when calcium phosphate and/or bioactive glass particles are added, the mixture may be a suspension. Alternatively, if a soluble calcium phosphate and/or bioactive additive is used, the mixture may be a solution. In some embodiments, the mixture may be viscous, such as a paste, which can be obtained by controlling the amount of polymer solution relative to calcium phosphate or bioactive additive, as well as the size of the particle component of the paste. A paste may be utilized, for example, when coating the mixture on a substrate. However, solutions or suspension of the mixture can also be used to coat substrates.

The amount of calcium phosphate and/or bioactive additive in the mixture may vary depending on the application. In some embodiments, the amount of calcium phosphate may range from about 15 to about 50 wt %, based on the total weight of the mixture. The total weight of the mixture may be the summed weight of the individual components of the mixture, such as calcium phosphate, bioactive additive, and polymer solution. In some embodiments, the amount of calcium phosphate may range from about 15 wt % to about 40 wt %, preferably about 20 wt % to about 40 wt %. In some embodiments, the mixture may be a paste, when calcium phosphate exceeds about 20 wt %. An amount of a bioactive additive present in the mixture may be dependent on the identity of the bioactive additive, and may range from about 0.001 wt % to about 80 wt % of the mixture. For example, a bioactive additive that is a growth factor may be present in a very low to low concentration, for example, ranging from about 0.001 wt % to about 10 wt % of the mixture. For example, a bioactive additive that is a structural component, such as collagen, may be present in a higher concentration, for example, ranging from about 10 wt % to about 80 wt % of the mixture.

The amount of polymer solution used relative to other components, such as the calcium phosphate and/or the bioactive additive, may influence the properties. For example, as shown in FIG. 2, for a 10 wt % PCL-GAA solution, an amount of calcium phosphate of at least about 19 wt %, relative to the 10 wt % PCL-GAA solution, can produce a scaffold that retains a shape of the mold in which the scaffold was made, and also retains the calcium phosphate. In contrast, below about 19 wt % in this exemplary embodiment, the scaffold fails to retain the shape of the mold, and at least some of the calcium phosphate.

The mixture may be formed in various ways. In some embodiments, the polymer solution and at least one of the calcium phosphate or bioactive additive can be combined to form the mixture, and then the mixture may be deposited on a substrate, in a mold, or in any suitable apparatus to shape a scaffold. In one embodiment, calcium phosphate is deposited in a mold, and then the polymer solution is added to the mold to form the mixture. In one embodiment, a substrate is dipped in the polymer solution, and then the coated substrate is dipped in, or otherwise coated with, calcium phosphate. Similar methods of forming a mixture can be applied for bioactive additives.

In some embodiments, the precipitating agent may be frozen in the calcium phosphate and/or bioactive additive. For example, prior to adding the calcium phosphate and/or bioactive additive to the polymer solution, the calcium phosphate and/or bioactive additive may be soaked with the precipitating agent, and frozen. The frozen calcium phosphate and/or bioactive additive may then be mixed with the polymer solution to form the mixture. The frozen calcium phosphate and/or bioactive additive will thaw in the mixture and release the precipitating agent which can result in precipitation of the polymer from the mixture to form a scaffold.

In some embodiments, the polymer solution may be frozen and then added to the precipitating agent. In other embodiments, the mixture of the polymer solution and calcium phosphate and/or the bioactive additive may be frozen and then added to the precipitating agent. For example, the polymer solution may be mixed with calcium phosphate and/or bioactive additive to form the mixture. The mixture may then be frozen, and then contacted with the precipitating agent. As the frozen mixture thaws, precipitation of the polymer can occur to form a scaffold.

In one embodiment, a scaffold may be formed with a bioactive additive that includes living cells. For example, such a scaffold may be used to deliver the living cells to tissues or implants. The living cells may be frozen in an appropriate freezing medium for cells. The frozen living cells may be further encased in a frozen solution containing sodium hydroxide or another base to form a frozen formulation. The frozen formulation could be submerged in the polymer solution to form the mixture. As the base and polymer mix to reach pH neutrality, polymer can precipitate around and encase the living cells to form a scaffold.

The method may comprise removing the solvent and/or precipitating agent from the scaffold. For example, after precipitation of the polymer the solvent may be removed from the resulting scaffold by any suitable method. In some embodiments, the precipitating agent may be removed when the solvent is removed. Removal of the solvent and/or precipitating agent may occur over any suitable time frame. This time frame may depend, for example, on the size of the scaffold, amount of solvent and/or precipitating agent used, the method of removal used, and the like. In some embodiments, removal of the solvent and/or precipitating agent may range up to about 24 hours. In some embodiments, removal of the solvent ranges from about 5 minutes to about 20 hours. In some embodiments, removal of the solvent ranges from about 5 minutes to about 15 hours. In some embodiments, removal of the solvent ranges from about 5 minutes to about 10 hours. In some embodiments, removal of the solvent ranges from about 5 minutes to about 5 hours. In some embodiments, removal of the solvent ranges from about 5 minutes to about 3 hours. In some embodiments, removal of the solvent ranges from about 20 minutes to about 1 hour. In yet other embodiments, removal of the solvent range from about 15 minutes to about 30 minutes. In one embodiment, the solvent may be removed by rinsing, which may result in dilution and removal of the solvent. For example, the scaffold may be submerged in water during the rinsing process. In one embodiment, the solvent may be removed by evaporating the solvent under room temperature and ambient pressure conditions. In other embodiments, removal of the solvent may be accelerated by exemplary processes, such as exposure to temperatures below the melting point of the polymer of the scaffold, and also below a temperature that may inactivate, denature, or otherwise destroy any other component of the scaffold, as well as ambient forced air, vacuum drying, lyophilization, or other methods that can remove the solvent but do not untowardly affect any other component of the scaffold. In one example, removal of a solvent in a PCL-containing scaffold may occur at temperatures below about 60° C. because PCL melts at about 60° C. The above-described methods for removal of the solvent may be used alone or in combination.

Further, for applications where the scaffold is used within the human body, sterilization may need to be performed. One common sterilization method is gamma-beam irradiation. Polymers, such as PCL, and calcium phosphate are amenable to gamma-beam irradiation. In some embodiments, gamma-beam irradiation may affect the molecular weight and/or other aspects of the chemical structure of the plastic comprising the scaffold and thus the physical characteristics of the scaffold even when polymers such as PCL are used. Therefore, parameters of the method, such as polymer concentration, molecular weight and the like, may be modified to account for a sterilization process.

The methods described herein can be further exemplified as discussed in the Examples below.

Scaffold

The scaffolds formed herein have significant porosity, allowing them to soak up and retain biological fluids like blood or bone marrow aspirate, which are often added to bone regeneration scaffolds prior to implantation in patients. Also, their lower density, foam-like composition makes them easier to mold by hand and compress to fit into a hole or defect in bone. It also may be speculated that the lower density, foam-like nature of the scaffolds described in the present invention may allow for their more rapid in vivo degradation and resorption in comparison with PCL-based scaffolds formed using other methods.

The scaffolds described herein are in the form of a polymer matrix. The scaffolds produced using the methods described herein may be different in terms of final composition and physical properties as compared with scaffolds manufactured by other methods. The scaffolds described herein may have a foam-like appearance. The scaffolds may have an relatively amorphous structure. The scaffolds may be non-crystalline. The density and porosity of the scaffolds can be controlled by the methods described herein to control a rate of bioresorption of the scaffold in vivo. In some embodiments, the plastic component(s) of the scaffolds produced using the methods discussed herein may not have a uniform or homogeneous fully interconnected pore structure. Moreover, in some embodiments, the scaffolds may have calcium phosphate and/or bioactive additive embedded in the polymer matrix. In some embodiments, though embedded in the polymer matrix, calcium phosphate and/or bioactive additive may retain at least some characteristic properties, such as porosity.

In some embodiments, the scaffold may be a polymer matrix, for example, made of only polymer and absent of additional materials embedded within the matrix and/or on the surface thereof, for example, as shown in FIG. 10 and discussed herein in Example 5-1. Such a scaffold may be utilized to hold open or expand a space prior to organ transplant, to inhibit or block tissue adhesions following surgery, or other medical applications that do not involve orthopedic applications, such as bone regeneration or bone replacement. Further, it is contemplated that such scaffolds may be utilized in non-medical applications, such as for thermal or electrical insulation, packing materials, or the like.

In some embodiments, the scaffold includes the polymer matrix and at least one of calcium phosphate or a bioactive additive embedded therein and/or disposed on the surface thereof. The calcium phosphate may be any number of calcium phosphate materials as discussed herein. The bioactive additive may be any number of additives, such as collagen, bioactive glass, and/or other additives as discussed herein. In some embodiments, the scaffold does not include any animal-derived materials, such as collagen, living cells, or other animal-derived materials. Among other reasons, the absence of animal-derived materials may prevent immunoreactivity, transmission of viral, bacterial, or prion infections and/or satisfy religious concerns in regards to animal-derived materials, when such scaffolds are implanted as medical devices into humans.

The scaffold may include a substrate. For example, the substrate may modify the physical properties of the scaffold, such as a three dimensional substrate formed from a stiff polymer to improve mechanical strength of the scaffold. Exemplary substrates may include a mesh or screen, such as those made of a metal, plastic, or fabric, a porous polymer substrate, a bone suture anchor, which may be filamentous and/or comprised of a textile, a porous metal implant, a tissue autograft or allograft or derivatives therefrom and/or living tissue.

The scaffold can have any suitable shape, for example, such as a sheet, a rectangle, a wedge, a cylinder, a square, a sphere, and the like, or the shape may be irregular, such as sized to fit a particular application, such as a size and/or shape of a portion of bone being filled. A mold, or another apparatus, such as a substrate, may be used to make a scaffold having any suitable shape.

Polymer

The polymer used in the methods described herein and scaffolds is not particularly limiting, though polymers that are biocompatible and can be dispersed and/or dissolved in a solvent are preferred.

Any suitable resorbable biocompatible polymer may be used in accordance with the present invention. Examples of suitable polymers include, without limitation, polycaprolactones (PCL), polyglycolides (PGA), polylactic acids (PLA), polyethylene, polypropylene, polystyrene, poly(D,L-lactic-co-glycolide) (PLGA), polyglycolic acid (PGA), poly-L-Lactic acid (PL-LA), polysulfones, polyolefins, polyvinyl alcohol (PVA), polyalkenoics, polyacrylic acids (PAA), polyesters, lower alkyl cellulose ethers, methylcellulose, sodium carboxymethyl cellulose, hydroxyethyl cellulose, hydroxypropyl cellulose, hydroxypropylmethylcellulose, carboxymethyl cellulose, and mixtures thereof. In other embodiments, the biocompatible polymer may further contain gelatin and other suitable polymers described, for example, in U.S. Pat. Nos. 7,189,263; 7,534,451; 7,531,004; and 8,287,915, which are incorporated herein by references in their entireties.

In some embodiments, the polymer may have a molecular weight (MW) ranging from about 3,000 g/mol to about 150,000 g/mol. In one embodiment, the polymer may have a MW ranging from about 3,000 g/mol to about 120,000 g/mol. In yet another embodiment, the polymer may have a MW ranging from about 3,000 g/mol to about 100,000 g/mol. In yet another embodiment, the polymer may have a MW ranging from about 3,000 g/mol to about 80,000 g/mol. In yet another embodiment, the polymer may have a molecular weight (MW) ranging from about 14,000 g/mol to about 65,000 g/mol. In one embodiment, the polymer may have a MW ranging from about 40,000 g/mol to about 50,000 g/mol. In some embodiments, molecular weights above 150,000 g/mol can be utilized. In some embodiments, the polymer may have a molecular weight ($M_n$) ranging from greater than about 45,000 g/mol up to about 80,000 g/mol. In some embodiments, $M_n$ above 80,000 g/mol can be utilized. For example, different polymers and different solvents can allow for polymers having higher MW to dissolve to form a polymer solution.

Calcium Phosphate

Various calcium phosphates are contemplated and include, for example, tetra-calcium phosphate, di-calcium phosphate, dicalcium phosphate dihydrous, dicalcium phosphate anhydrous, tri-calcium phosphate, mono-calcium phosphate, β-tricalcium phosphate, α-tricalcium phosphate, oxypatite, hydroxypatite, and mixtures thereof. However, for the sake of brevity, "calcium phosphate" includes any calcium salt known to those skilled in the art. The preparation of various forms of calcium phosphate for use in the present invention is described in U.S. Pat. Nos. 5,939,039, 6,383,519, 6,521,246, and 6,991,803, which are incorporated herein by references in their entireties. Exemplary calcium phosphate products may include Vitoss® Bone Graft Substitutes, such as Vitoss® micromorsels (1-2 mm) or Vitoss® subfines (<1 mm) (Stryker Orthobiologics, Malvern, Pa.).

Some embodiments of the scaffold may partially comprise materials, or morsels, resulting from an oxidation-reduction reaction. These materials may be produced by methods comprising preparing an aqueous solution of a metal cation and at least one oxidizing agent. The solution is augmented with at least one soluble precursor anion oxidizable by said oxidizing agent to give rise to the precipitating agent oxoanion. The oxidation-reduction reaction thus contemplated is conveniently initiated by heating the solution under conditions of temperature and pressure effective to give rise to said reaction. The oxidation-reduction reaction can cause at least one gaseous product to evolve and the desired intermediate precursor mineral to precipitate from the solution. A reactive blend may be imbibed into a material that is capable of absorbing it to produce a porous mineral. It may be preferred that the material have significant porosity, be capable of absorbing significant amounts of the reactive blend via capillary action, and that the same be substantially inert to reaction with the blend prior to its autologous oxidation-reduction reaction.

The intermediate precursor mineral thus prepared can either be used "as is" or can be treated in a number of ways. Thus, it may be heat-treated greater than about 800° C. or, preferably, greater than about 1100° C. in accordance with one or more paradigms to give rise to a preselected crystal structure or other preselected morphological structures therein. In some embodiments, the oxidizing agent is nitrate ion and the gaseous product is a nitrogen oxide, generically depicted as $NO_x(g)$. The precursor mineral provided by the present methods be substantially homogenous. As used in this context, substantially homogenous means that the porosity and pore size distribution throughout the precursor mineral is the same throughout.

In some embodiments, the intermediate precursor mineral may be any calcium salt. Subsequent modest heat treatments convert the intermediate material to, e.g., novel monophasic calcium phosphate minerals or novel biphasic β-tricalcium phosphate (β-TCP)+type-B, carbonated apatite (c-HAp) [β-$Ca_3(PO_4)_2$+$Ca_5(PO_4)_{3-x}(CO_3)x(OH)$] particulates. More preferably, the heat treatment converts the intermediate material to a predominantly β-TCP material.

In one embodiment, the calcium phosphate is □-TCP. In some embodiments, the calcium phosphate is porous. In some embodiment, the calcium phosphate contains micro-, meso-, and macroporosity. In some embodiment, the porosity of the calcium phosphate is interconnected. Macroporosity is characterized by pore diameters greater than about 100 µm and, in some embodiments, up to about 1000 µm to 2000 µm. Mesoporosity is characterized by pore diameters between about 10 µm and 100 µm, while microporosity occurs when pores have diameters below about 10 µm. In some embodiments, that macro-, meso-, and microporosity occur simultaneously and are interconnected in products. It is not necessary to quantify each type of porosity to a high degree. Rather, persons skilled in the art can easily determine whether a material has each type of porosity through examination, such as by mercury intrusion porosimetry, helium pycnometry or scanning electron microscopy. While it is certainly true that more than one or a few pores within the requisite size range are needed in order to characterize a sample as having a substantial degree of that particular form of porosity, no specific number or percentage is called for. Rather, a qualitative evaluation by persons skilled in the art shall be used to determine macro-, meso-, and microporosity.

In some embodiments, the calcium phosphate is in the form of particles or morsels and may contain a porous structure as described herein.

It will be appreciated that in some embodiments, the overall porosity of the calcium phosphate will be high. This characteristic is measured by pore volume, expressed as a percentage. Zero percent pore volume refers to a fully dense material, which, perforce, has no pores at all. One hundred percent pore volume cannot meaningfully exist since the same would refer to "all pores" or air. Persons skilled in the art understand the concept of pore volume, however and can easily calculate and apply it. For example, pore volume may be determined in accordance with Kingery, W. D., Introduction to Ceramics, Wiley Series on the Science and Technology of Materials, $1^{st}$ Ed., Hollowman, J. H., et al. (Eds.), Wiley & Sons, 1960, p. 409-417, which provides a formula for determination of porosity. Expressing porosity as a percentage yields pore volume. The formula is: Pore Volume=$(1-f_p)$ 100%, where $f_p$ is fraction of theoretical density achieved.

Porosity can be measured by Helium Pycnometry. This procedure determines the density and true volume of a sample by measuring the pressure change of helium in a calibrated volume. A sample of known weight and dimensions is placed in the pycnometer, which determines density and volume. From the sample's mass, the pycnometer determines true density and volume. From measured dimensions, apparent density and volume can be determined. Porosity of the sample is then calculated using (apparent volume-measured volume)/apparent volume. Porosity and pore size distribution may also be measured by mercury intrusion porosimetry.

Pore volumes in excess of about 30% may be achieved while materials having pore volumes in excess of 50% or 60% may also be routinely attainable. Some embodiments of the calcium phosphate may have pore volumes of at least about 70%. Some embodiments that may be preferred have pore volumes in excess of about 75%, with 80% being still more preferred. Some embodiments may have pore volume greater than about 90%, more preferably greater than about 92%. In some preferred cases, such high pore volumes are attained while also attaining the presence of macro- meso- and microporosity as well as physical stability of the materials produced.

It will be appreciated that the morsel size and content will be selected based on the desired application. For example, it may be necessary for the scaffold to have one or more properties, such as elasticity, stiffness, tensile strength, and in vivo degradation rate. Morsel size and content of the morsels within the scaffold may be selected with one or more of those properties in mind. The morsel size can range from about 100 µm to 2,000 µm, from about 200 µm to 900 µm, and from about 212 µm to about 850 µm. Unless otherwise specified, morsel size as used herein refers to the sieve size used to partition the calcium phosphate morsels.

Due to the high porosity and broad pore size distribution (1 µm to 2000 µm) of the morsels, the scaffold may be able to wick/soak/imbibe materials very quickly, and also be capable of retaining them. Materials may include a variety of fluids including blood, bone marrow aspirate, saline, antibiotics and proteins such as bone morphogenetic proteins (BMPs). Materials can also be imbibed with cells (e.g., fibroblasts, mesenchymal, stromal, marrow and stem cells), platelet rich plasma, other biological fluids, and any combination of the above. The scaffold can hold, maintain, and/or retain fluids once they are imbibed, allowing for contained, localized delivery of imbibed fluids. This capability has utility in cell-seeding, drug delivery, and delivery of biologic molecules as well as in the application of bone tissue engineering, orthopedics, and carriers of pharmaceuticals.

Bioactive Additive

Various bioactive additives are contemplated, including natural and synthetic bioactive additives. Exemplary bioactive additives may include bioactive glass, bone chips, demineralized bone chips or powder, living cells, lyophilized bone marrow, collagen, other bioactive proteins or growth factors, biologics, peptides, glycosaminoglycans, anti-inflammatory compounds, antibiotics, anti-microbial elements, small biomolecules, active pharmaceutical ingredients, antibodies, and/or mixtures thereof.

The type of collagen used is not particularly limiting, and can include native fibrous insoluble human, bovine, porcine, or synthetic collagen, soluble collagen, reconstituted collagen, or combinations thereof. Some embodiments of the scaffolds do not contain collagen.

"Bioactive glass" as used herein may be any alkali-containing ceramic, glass, glass-ceramic, or crystalline material that reacts as it comes in contact with physiologic fluids including, but not limited to, blood and serum, which leads to bone formation. In some embodiments, bioactive glasses, when placed in physiologic fluids, form an apatite layer on their surface. Examples of bioactive glasses suitable for use are described in U.S. Pat. No. 5,914,356, incorporated herein by reference. Suitable bioactive materials also include 45S5 glass and glass-ceramic, 58S5 glass, S53P4 glass, apatite-wollastonite containing glass and glass-ceramic. The bioactive glass may be a glass-ceramic composition comprising heterogeneous particles having an irregular morphology and regions of combeite crystallites ("Combeite glass-ceramic" having the chemical composition $Na_4Ca_3Si_6O_{16}(OH)_2$). In some embodiments, the bioactive glass comprises about 5-50% by volume of regions of combeite crystallites. Bioactive glasses suitable for use may be those compositions comprising calcium-phosphorous-sodium-silicate and calcium-phosphorous-silicate. Such bioactive glasses include NovaBone and NovaBone-AR, distributed by NovaBone Products, LLC, Alachua, Fla. Further bioactive glass compositions that may be suitable for use are described in U.S. Pat. No. 6,709,744, which is incorporated herein by reference.

In some embodiments, resorption of bioactive glass particles of about 150 µm or less occurs as silica as released within the apatite gel layer, while larger particles are eventually broken down by osteoclasts (Goasin, A. Bioactive Glass for Bone Replacement in Craniomaxillofacial Reconstruction, Plastic and Reconstructive Surgery (2004) Vol. 114, No. 2, pp. 590-593). The scaffold may provide appropriate bone growth independent of the inclusion of bioactive glass. The role of the bioactive glass in the scaffold described herein may be stimulatory to osteoblasts, and as such, large particles of glass (>150 µm) may not be necessary, and thus the particles which are resorbed via dissolution are preferred. However, all sizes of resorbable glass particles are contemplated as suitable.

Particle size measurement is well known in the art. Unless otherwise specified, particle size as used herein refers to the sieve size used to partition the glass particles. The bioactive glass particles may range in size from about 20 µm to about 200 µm, or about 100 µm or less, or about 150 µm or less, or about 30 µm to about 200 µm. The bioactive glass particles may be bimodal in nature, with distinct particles in the size range 32 µm-90 µm and particles in the size range 90 µm-150 µm. The bioactive glass particles may be solid or may even be porous. In some embodiments, the bioactive glass is nonporous.

EXAMPLES

Experimental Example 1

Scaffold Quality as a Function of Polymer Concentration

Figure 1B:
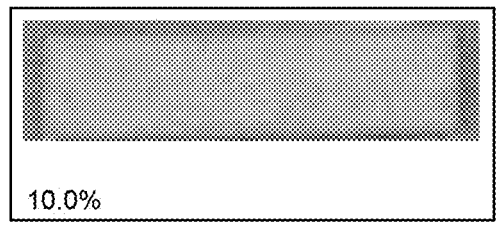
Figure 1C:
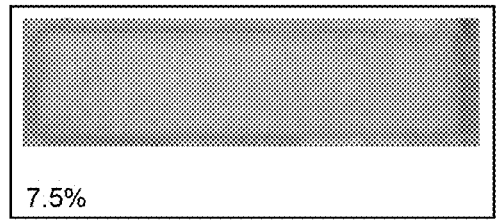
Figure 1D:
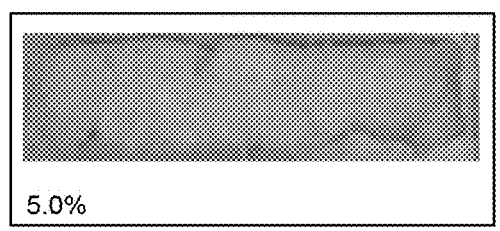

Experimental Example 1 studies scaffold quality as a function of polymer concentration in the polymer solution. Examples 1-1 through 1-3, the results of which are depicted in FIGS. 1A-C, were made using the same methods, except different concentrations of polymer are used in the polymer solution in each Example. Comparative Example 1-1, the result of which is depicted in FIG. 1D, was made using the same methods, except using a polymer concentration lower than that of Examples 1-1 through 1-3.

A PCL filament-derived material for 3D printing (available from Makerbot, $M_n$=about 50,000 g/mol) The PCL filament-derived material was cut into small pieces prior to further use. Though the Examples herein used PCL filament-derived material, other types of PCL materials may be contemplated, for example, such as PCL pellets.

Example 1-1

Saturated PCL Solution

About 1.5 gram of PCL was added to about 10 g of glacial acetic acid (GAA) in a 50 ml plastic sample tube and the mixture was agitated over the course of several hours by intermittently vortexing using a Fisher Scientific Vortex Mixer to form a PCL solution. Other forms of mixing or sample agitation may be contemplated to solubilize the PCL. The PCL-GAA solution has a concentration of PCL greater than about 10 wt % and less than about 15 wt %. Concurrently, about 3.4 g of calcium phosphate (Vitoss® micromorsels, 1-2 mm, available from Stryker Orthobiologics) were placed into a mold (Aluminum, rectangular shaped, about 1.0 inch wide×4.0 inches long×7/16 inches deep), where the mold was sprayed with cooking oil and excess oil wiped away with a kimwipe prior to adding the calcium phosphate. About 12 g of the 10 wt %-15 wt % PCL-GAA solution was added to the mold containing the calcium phosphate, and the mixture of PCL, GAA, and calcium phosphate was allowed to sit for about 5 min in the mold. After which, about 1 to about 2 grams of water was added drop wise to the surface of the mixture, and the mixture was allowed to incubate for about 15 to about 30 minutes at room temperature and ambient pressure conditions. After the incubation period, the mold was submerged to about 1 to about 2 mm below the surface of a water bath at about room temperature and allowed to incubate for about 15 to about 30 minutes. After the incubation period, and while submerged, the lateral edges of the scaffold were separated from the mold using a metal spatula. The mold and scaffold were further incubated for about 15 to 30 minutes. After the incubation period the scaffold was removed from the mold and air dried. The scaffold lost more than twice its weight during drying. The resulting scaffold is depicted in FIG. 1A.

Example 1-2

10% PCL Solution

Example 1-2 is made using the same procedure described for Example 1-1, except about 1 g of PCL is added to about 10 g of GAA to form a 10 wt % PCL-GAA solution. The resulting scaffold is depicted in FIG. 1B.

Example 1-3

7.5% PCL Solution

Example 1-3 is made using the same procedure described for Example 1-1, except about 0.75 g of PCL is added to about 10 g of GAA to form a 7.5 wt % PCL_GAA solution. The resulting scaffold is depicted in FIG. 1C.

Comparative Example 1-1

5.0% PCL Solution

Comparative Example 1-1 is made using the same procedure described for Example 1-1, except about 0.5 g of PCL is added to about 10 g of GAA to form a 5 wt % PCL-GAA solution. The resulting scaffold is depicted in FIG. 1D.

As shown in FIG. 1A-D, the scaffolds of Examples 1-1 through 1-3, and Comparative Example 1-1 have bright white, styrofoam-like appearance, and in some cases exhibit a fluffy, sea-foam like surface. The scaffolds roughly approximate the size of the mold from which the scaffolds were cast.

The concentration of PCL in the polymer solutions was found to affect the physical characteristics of the resulting scaffold. Intact scaffolds, e.g., those that could easily be removed from the mold and retained a large fraction of the calcium phosphate added, were produced using 10 wt %-15 wt %, 10 wt %, and 7.5 wt % PCL-GAA solutions as shown in FIGS. 1A-C.

Scaffolds were assessed qualitatively for moldability by wetting them with physiologic saline and hand kneading for one to two minutes. Scaffolds were qualitatively assessed to see if they resisted hand-molding and if so, to what extent; whether they could be torn apart by hand, and after molding if they remained cohesive; e.g., did the polymer matrix remain intact and retain a large fraction of the calcium phosphate.

The scaffolds of Examples 1-1 and 1-2 could be torn apart by hand, were relatively stiff and only slightly moldable, however the scaffolds remained intact and retained most if not all of the calcium phosphate. The scaffold of Example 1-3 could be torn apart by hand, were absorbent and partially moldable, their polymer matrix remained intact but lost some calcium phosphate during hand-kneading. The scaffold of Comparative Example 1-1 could be torn apart by hand, however, the polymer matrix did not remain intact upon de-molding and lost calcium phosphate easily upon de-molding.

Experimental Example 2

Scaffold Quality as a Function of Amount of Polymer Solution

Figure 2A:
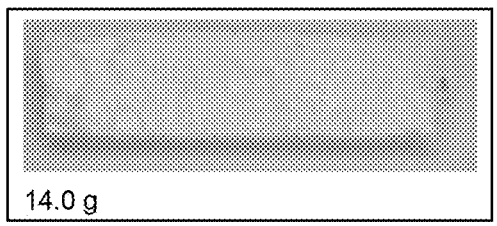
FIGS. 2A-F depict scaffolds made using a range of amounts of a polymer solution in accordance with some embodiments of the present invention.
Figure 2B:
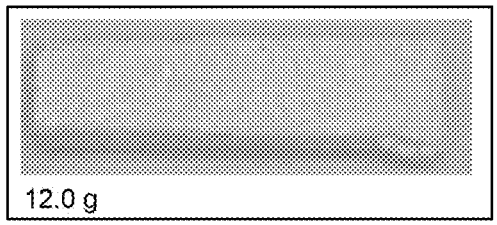
Figure 2C:
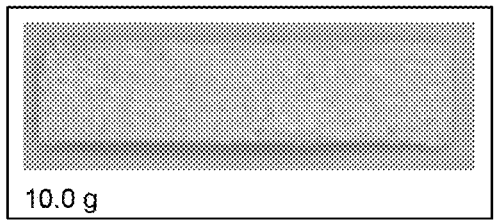
Figure 2D:
Figure 2E:
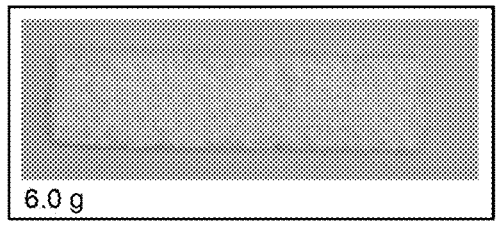
Figure 2F:

Experimental Example 2 studies scaffold quality as a function of amount of polymer solution. Examples 2-1 through 2-3, the results of which are depicted in FIGS. 2A-C, were made using the same methods, except different amounts of polymer solution were used in each Example. Comparative Examples 2-1 through 2-3, the results of which are depicted in FIGS. 2D-F, were made using the same methods, except using a polymer concentration lower than that of Examples 2-1 through 2-3. Examples 2-1 through 2-3 and Comparative Examples 2-1 through 2-3 were performed using PCL filament-derived material as used in Experimental Example 1.

Example 2-1

14 g Polymer Solution

A scaffold of Example 2-1 was prepared in the same manner as that of Example 1-2, using a 10 wt % PCL-GAA solution, except using 14 g of 10 wt % PCL-GAA solution. The resulting scaffold is depicted in FIG. 2A.

Example 2-2

12 g Polymer Solution

A scaffold of Example 2-2 was prepared in the same manner as that of Example 1-2. The resulting scaffold is depicted in FIG. 2B.

Example 2-3

10 g Polymer Solution

A scaffold of Example 2-3 was prepared in the same manner as that of Example 1-2, using a 10 wt % PCL-GAA solution, except using 10 g of the 10 wt % PCL-GAA solution. The resulting scaffold is depicted in FIG. 2C.

Comparative Example 2-1

8 g Polymer Solution

A scaffold of Comparative Example 2-1 was prepared in the same manner as that of Example 1-2, using a 10 wt % PCL-GAA solution, except using 8 g of the 10 wt % PCL-GAA solution. The resulting scaffold is depicted in FIG. 2D.

Comparative Example 2-2

6 g Polymer Solution

A scaffold of Comparative Example 2-2 was prepared in the same manner as that of Example 1-2, using a 10 wt % PCL-GAA solution, except using 6 g of the 10 wt % PCL-GAA solution. The resulting scaffold is depicted in FIG. 2E.

Comparative Example 2-3

4 g Polymer Solution

A scaffold of Comparative Example 2-3 was prepared in the same manner as that of Example 1-2, using a 10 wt % PCL-GAA solution, except using 4 g of the 10 wt % PCL-GAA solution. The resulting scaffold is depicted in FIG. 2F.

The scaffolds of Examples 2-1 through 2-3, having about 10 g or greater of 10 wt % PCL-GAA solution, exhibited robust and cohesive properties as shown in FIG. 2A-C. However, the scaffolds of Comparative Examples 2-1 through 2-3, having about 8 g or less of 10 wt % PCL-GAA solution, were less robust and cohesive, and exhibited loss of at least calcium phosphate upon de-molding. In some cases, such as Comparative Example 2-3, the scaffold additionally exhibited a loss of structure upon de-molding as shown in FIG. 2F.

Experimental Example 3

Scaffolds Using Other Polymers and Solvents

Experimental Example 3 studies biodegradable or non-biodegradable polymers, other than those polymers used in Experimental Examples 1 and 2, which may be used to create scaffolds.

Example 3-1

Poly(D,L-Lactic-Co-Glycolide) in Acetone

Figure 3:
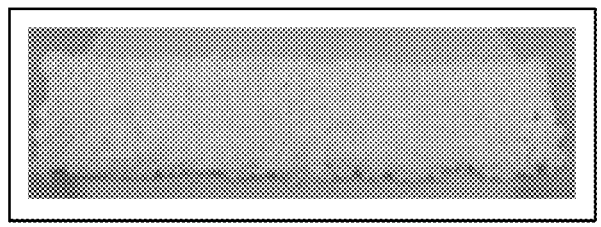
FIG. 3 depicts a scaffold in accordance with one embodiment of the present invention.

A scaffold of Example 3-1 was made from a polymer solution where about 1.7 g of poly (DL-lactic-co-glycolide) (50:50) (Available from Sigma Aldrich Chemicals) was dispersed in about 12 g Acetone. The polymer solution was added to a mold which included about 3.4 g of calcium phosphate (Vitoss® micromorsels, available from Stryker Orthobiologics). The scaffold was prepared using water as a precipitating agent as described in Experimental Example 1. The scaffold of Example 3-1 exhibited poor integrity as shown in FIG. 3. It is possible that increasing the concentration of polymer in the polymer solution, similar to results obtained in Experimental Example 1, may yield a scaffold having more desirable properties.

Experimental Example 4

Scaffold Including a Substrate

Scaffolds were prepared using various substrates, such as screens, porous polymer implants, three dimensional substrates, and bone suture anchors.

Example 4-1

Scaffold Including a Screen

Figure 4:
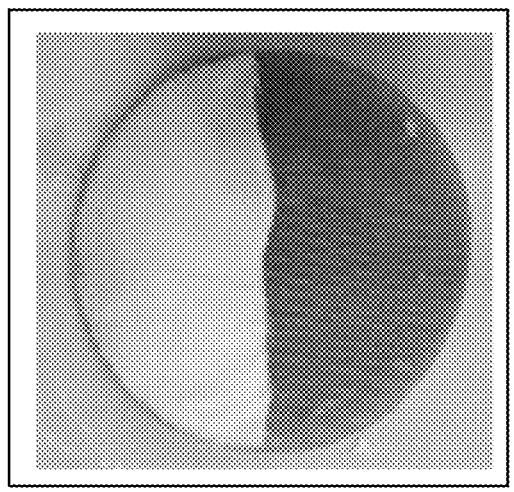
FIG. 4 depicts a scaffold in accordance with another embodiment of the present invention.

A paste was made from a mixture of a polymer solution (10 wt % PCL-GAA) and calcium phosphate (Vitoss® subfine, further sieved to obtain about 250 μm average particle size) in a weight ratio of about 1.0:1.5-2.0. Using a metal spatula, the paste was smeared on both sides of a stainless steel metal screen to cover about one half the surface area of the screen (316 Stainless, 50-100 mesh), and then immersed in water for about 15 to 30 seconds to precipitate the PCL leaving a PCL-calcium phosphate layer adhered to, and covering both sides of the metal screen as shown in FIG. 4.

Example 4-2

Scaffold Including Porous Polymer Implants

Figure 5A:
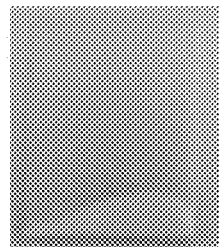
FIGS. 5A-D depict scaffolds in accordance with some embodiments of the present invention.
Figure 5B:
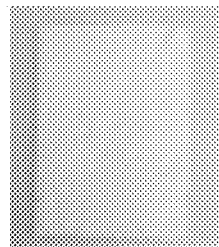
Figure 5C:
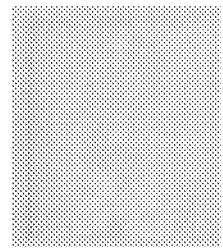
Figure 5D:
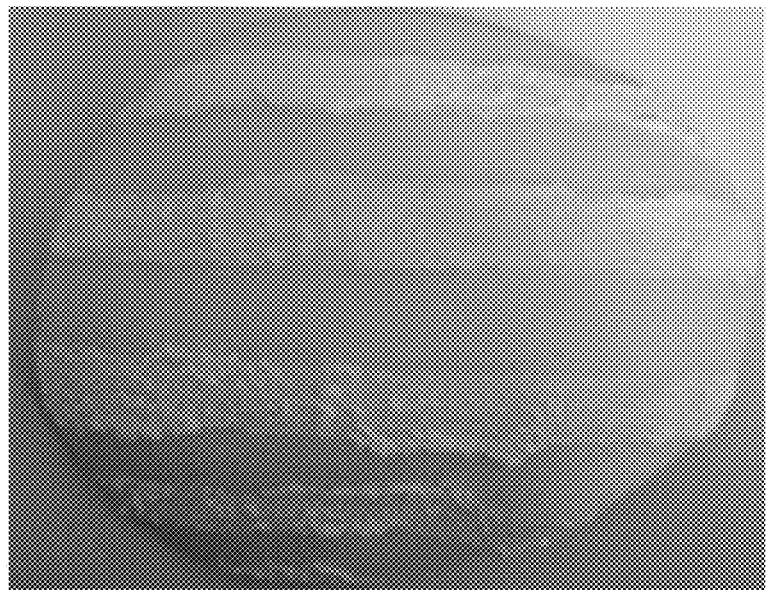

As shown in FIGS. 5A-D, scaffolds can be formed using porous high density polyethylene (HDPE) sheets as substrates (FIGS. 5A-C) or HDPE cranial implants (MedPor, FIG. 5D)

The scaffolds show in FIGS. 5A-B, D were made using PCL as a polymer and calcium phosphate (Vitoss® particles, about 250 μm). In the scaffold depicted in FIG. 5C, bioactive glass was substituted in place of calcium phosphate. The scaffolds of FIG. 5A-D were manufactured by one of three methods: (1) immersing the materials in a coating solution including 10% PCL-GAA and one of calcium phosphate or bioactive glass, (2) depositing the coating solution onto the substrates, for example, using a brush or another deposition device, or (3) immersing the substrates in a 10% PCL-GAA solution, and then dipping the wetted substrates in one of calcium phosphate or bioactive glass. In each method, the coated substrates were then submerged under water for about 15 to about 30 seconds to precipitate the polymer to form the scaffold.

In FIG. 5A, a porous HDPE sheet was dipped in a 10 wt % PCL-GAA solution including calcium phosphate at the bottom edge, and then precipitated, resulting in a small, uneven area coated a scaffold. In FIG. 5B, a porous HDPE sheet was immersed in 10% PCL-GAA, and then the surface of the porous HDPE sheet was pressed against a dry bed of calcium phosphate particles. It was then immersed in water to precipitate the scaffold, resulting in the entire surface coated with, and white from, calcium phosphate. In FIG. 5C, a porous HDPE sheet was coated similar to that of the sheet in FIG. 5B, except bioglass (Combeite, 90-150 microns) was used instead of calcium phosphate. The sheet shown in FIG. 5C is completely coated with a PCL-bioglass scaffold but is not bright white like a scaffold made of PCL and calcium phosphate since the bioglass is clear to moderately cloudy but translucent, and not an opaque white.

Example 4-3

Scaffold Including Three-Dimensional Substrate

Figure 6A:
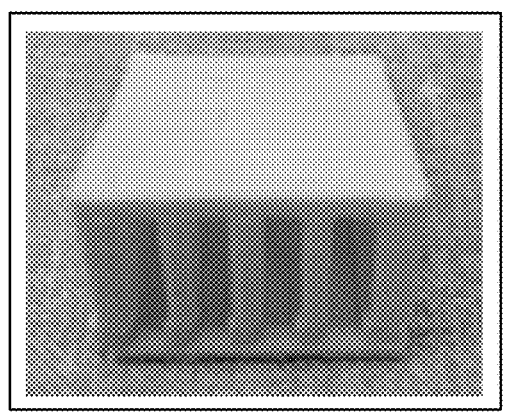
FIG. 6A depicts a substrate in accordance with some embodiments of the present invention.
Figure 6B:
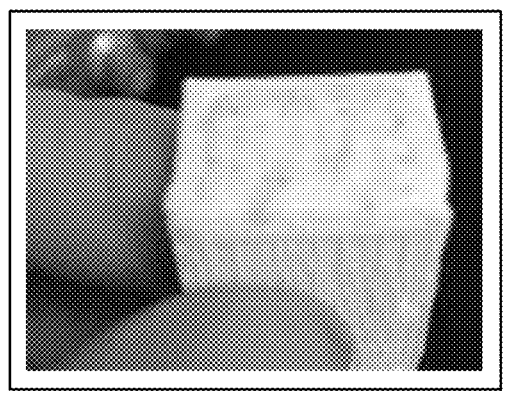
FIG. 6B depicts a scaffold including the substrate of FIG. 6A in accordance with some embodiments of the present invention.

Example 4-3 uses a polylactic acid (PLA) wedge as a substrate as shown in FIG. 6A. The PLA has been 3D printed, and has a cage configuration with a slotted base. A 10% PCL-GAA calcium phosphate (Vitoss® micromorsel suspension) was prepared in the same manner as described in Example 4-1, and packed into the interstices of the PLA wedge. The packed PLA wedge was submerged in a water bath for about 15 to about 30 sec, and then air dried. The resulting scaffold comprised a stiff cage of PLA in which a matrix of PCL embedded with calcium phosphate was stably incorporated throughout as shown in FIG. 6B.

Example 4-4

Scaffold Including Bone Suture Anchors

Figure 7A:
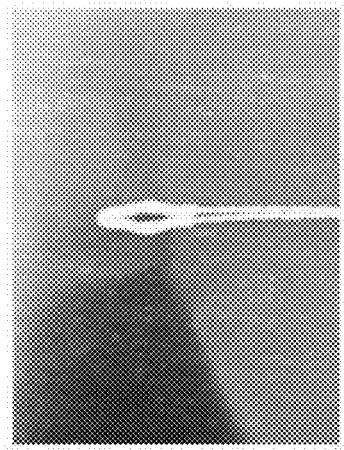
FIG. 7A depicts a substrate in accordance with some embodiments of the present invention.

As shown in FIG. 7A, a scaffold can include a bone suture anchor as a substrate. For example, one exemplary bone suture anchor is ICONIX™ bone suture anchors, available from Stryker, Inc.

The scaffolds of Example 4-4 are prepared using a PCL-GAA-calcium phosphate mixture or a PCL-GAA-bioactive glass mixture, each used in same proportions as for other pastes described in Example 4-1, were used to coat ICONIX bone suture anchors. The bone suture anchors are then dipped into the mixtures to coat the anchors with the mixture. The coated anchors are then submerged in a water bath for about 15 to about 30 seconds to precipitate the polymer to form the scaffold, and then air dried.

Figure 7B:
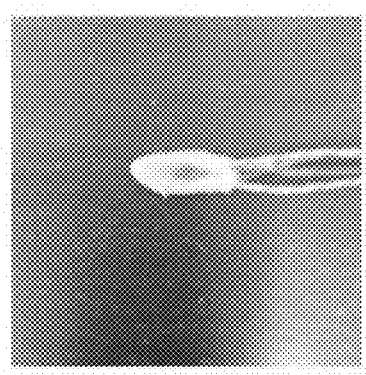
FIG. 7B depicts a scaffold including the substrate of FIG. 7A in accordance with some embodiments of the present invention.
Figure 7C:
FIG. 7C depicts a scaffold including the substrate of FIG. 7A in accordance with some embodiments of the present invention.
Figure 7D:
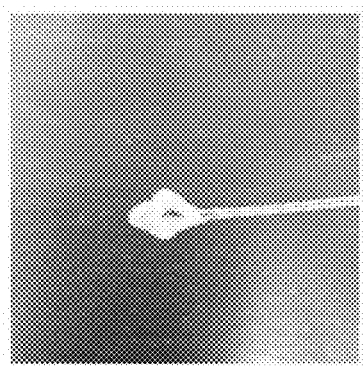
FIG. 7D depicts a scaffold including the substrate of FIG. 7A in accordance with some embodiments of the present invention.
Figure 8:
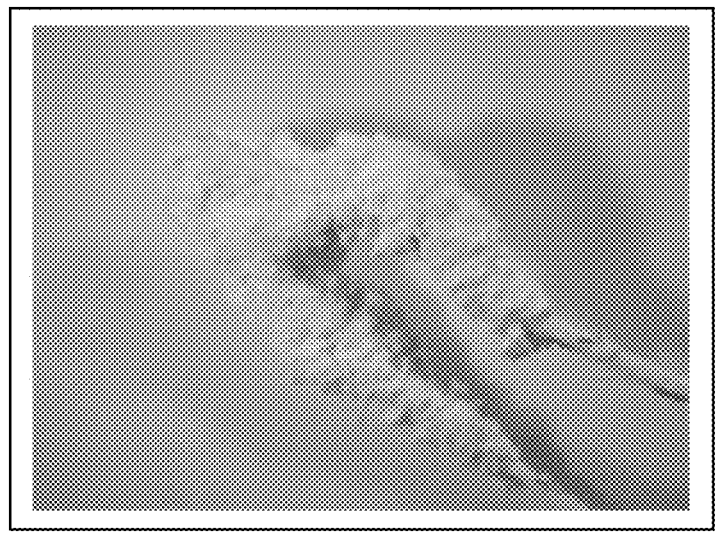
FIG. 8 depicts high magnification image of the scaffold depicted in FIG. 7B.

As shown in FIG. 7, a PCL-calcium phosphate (FIGS. 7B, 7D or PCL-bioactive glass scaffold (FIG. 7C) including a bone suture anchor as a substrate can be formed. At low magnification (FIGS. 7B-D), the scaffolds appeared as thick white to white-gray coatings on the bone suture anchor. As shown in FIG. 7D, the scaffolds have sufficient flexibility to be 'bunched', i.e., the bone suture anchor is subjected to a manipulation that results in it having a different configuration. At high magnification (FIG. 8), scaffolds having bone suture anchors coated with PCL-calcium phosphate exhibited a surface with a jagged profile. The jagged profile may be caused by the calcium phosphate, which can have a particulate form.

Figure 9A:
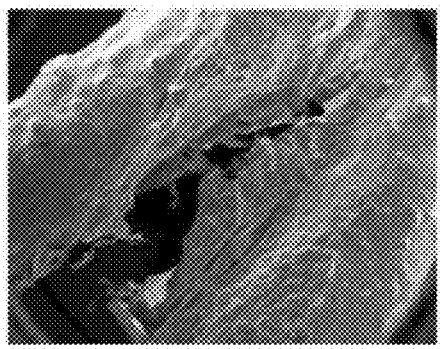
FIG. 9A depicts a scanning electron microscopy (SEM) image of the scaffold of FIG. 7C.
Figure 9B:
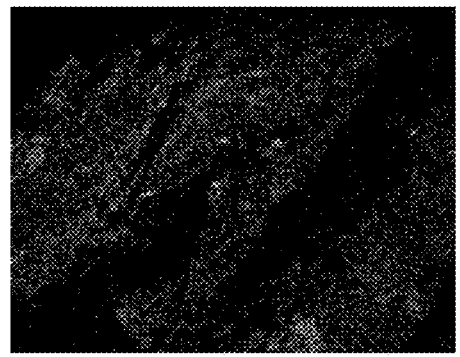
FIG. 9B depicts an EDAX (energy dispersive x-ray) chemical map of the SEM image of FIG. 9A.
Figure 9C:
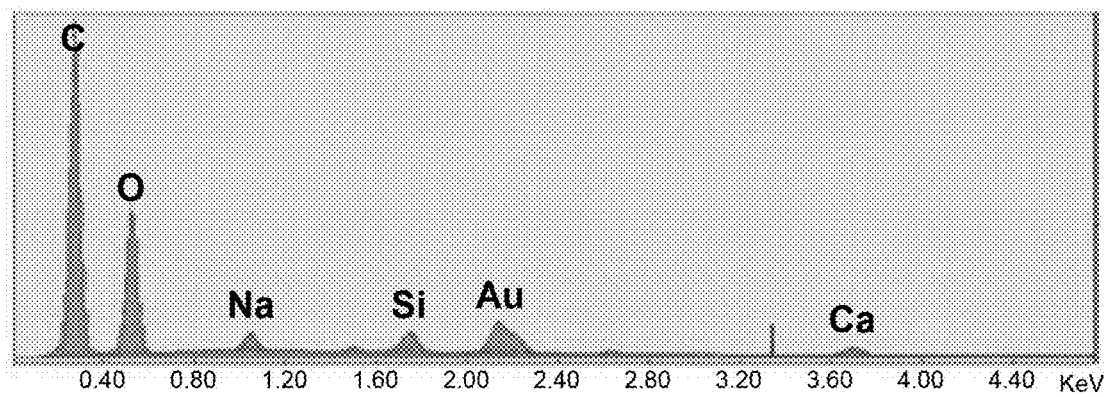
FIG. 9C depicts EDAX data of the scaffold of FIG. 7C.

At low magnification (FIG. 7C, FIG. 9A) bioactive glass particles in scaffolds having bone suture anchors coated with PCL-bioactive glass were too small to resolve. However, Energy-dispersive X-ray spectroscopy (EDAX) analysis (FIG. 9B, EDAX silicon map of FIG. 9A; FIG. 9C) of the PCL-bioactive glass scaffolds show elements consistent with both PCL (carbon and oxygen) and bioglass (calcium and silicon).

Experimental Example 5

Fine Structure and Atomic Composition of Scaffold

Experimental Example 5 examines fine structure and atomic composition of scaffolds made with and without calcium phosphate by scanning electron microscopy (SEM) and EDAX, respectively.

Example 5-1

PCL Scaffold

Figure 10A:
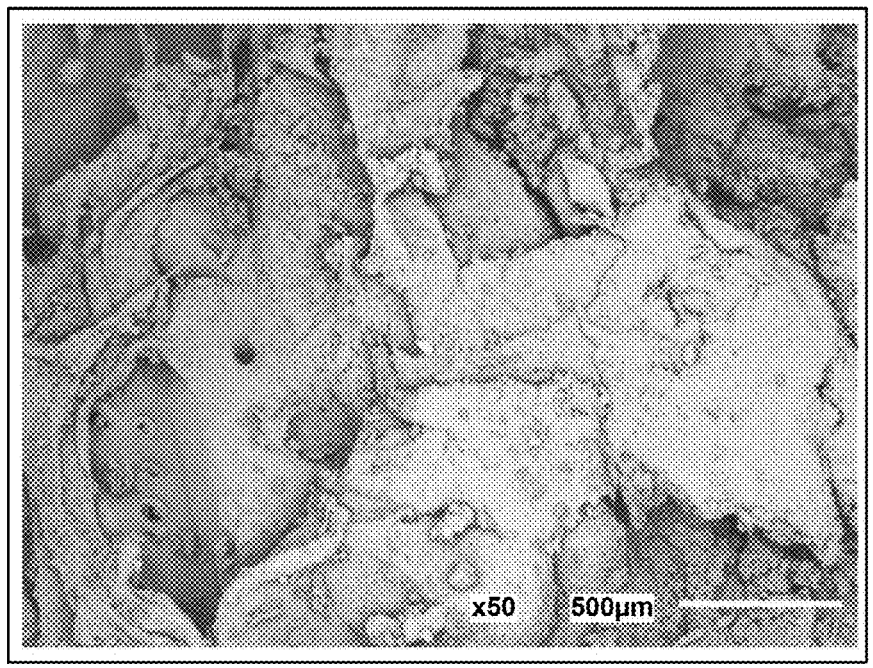
FIG. 10A-B depict SEM images of a scaffold in accordance with some embodiments of the present invention.
Figure 10B:
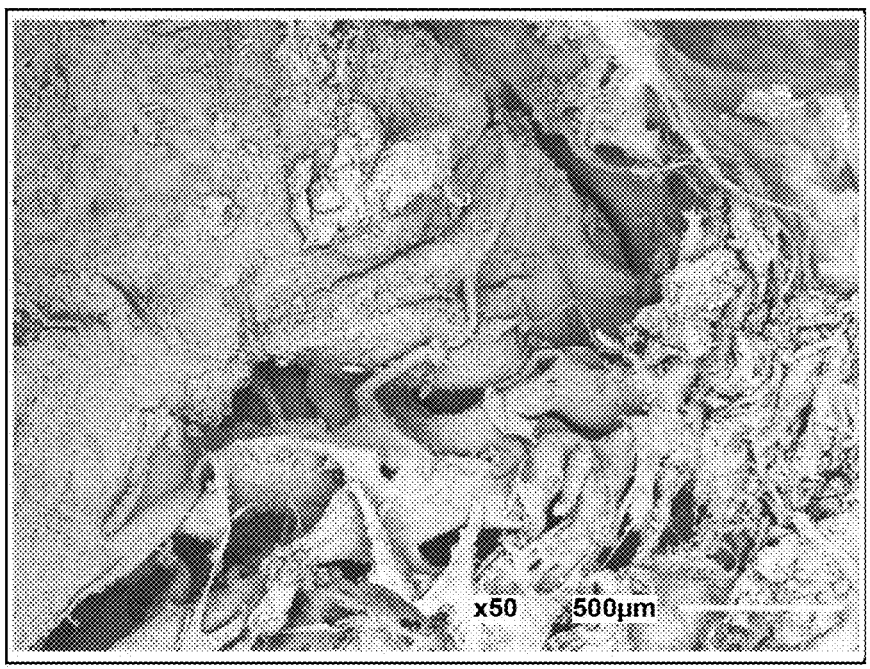

Example 5-1 is made in the same manner as Example 1-3, except calcium phosphate is omitted. The scaffold of Example 5-1 had a sheet-like, porous appearance overall (FIG. 10A), in some areas appearing to be comprised of multiple layers, with some fibrous or fiber-like structures (FIG. 10B) that were of irregular diameters. Varying numbers of large and small pores were also evident in many areas of the scaffold surface (FIG. 10). There was no evidence of a nano-fibrillar PCL composition as is characteristic of scaffolds fabricated by electrospinning of solubilized PCL.

Figure 11:
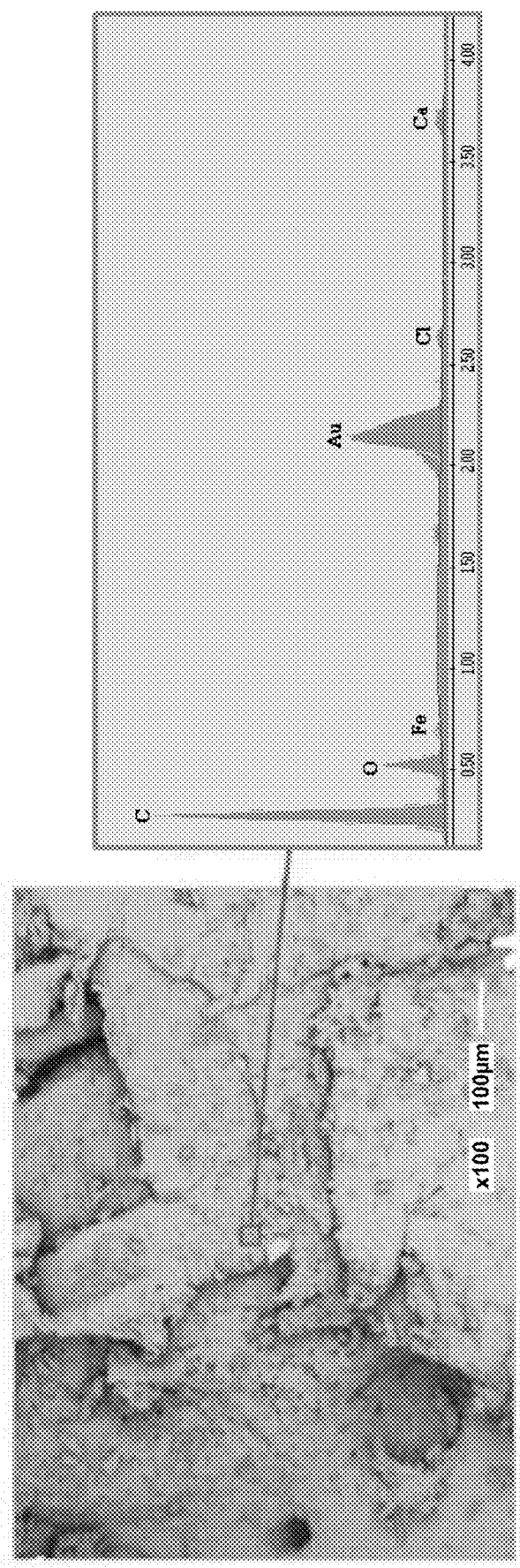
FIG. 11 depicts EDAX data from a region of the scaffold depicted in FIG. 10A.

EDAX analysis (FIG. 11) of a region of the scaffold shown in FIG. 10A showed that the majority of the scaffold was comprised of carbon and oxygen, which was as expected for a scaffold made from a PCL solution. Some salts were present in small quantities, which is attributed to reagents used to make the scaffold. The presence of gold is due to sputter-coating the scaffold with gold during SEM sample preparation.

Example 5-2

PCL-Calcium Phosphate Scaffold

Figure 12:
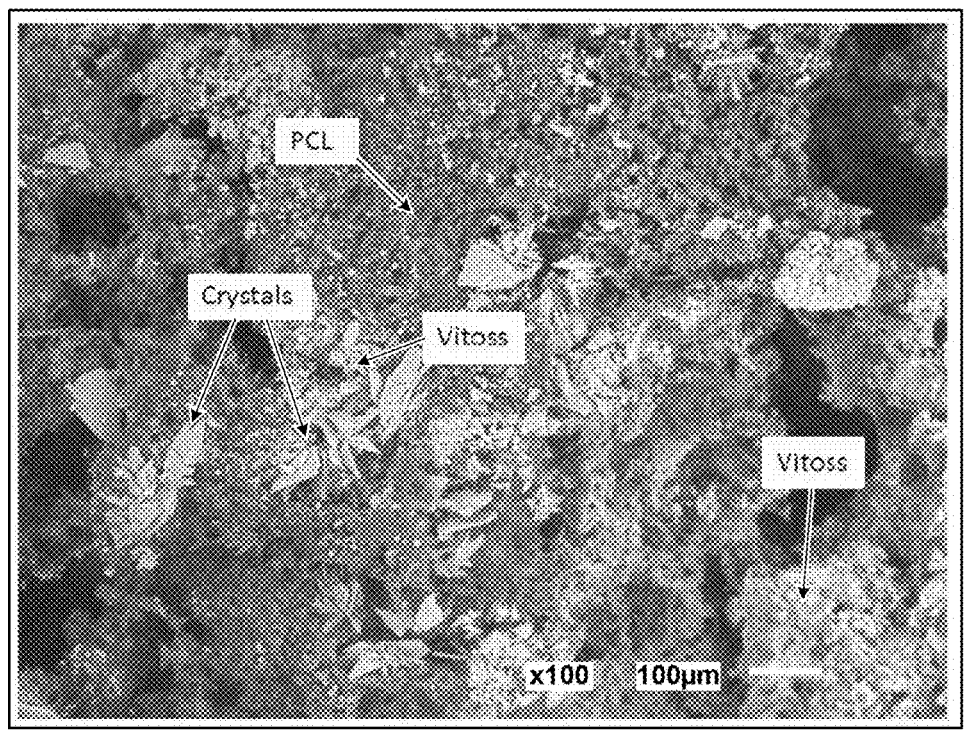
FIG. 12 depicts an SEM image of a scaffold in accordance with some embodiments of the present invention.

Example 5-2 is made in the same manner as Example 1-3. The scaffold of Example 5-2 showed similar scaffold morphology to that of Example 5-1, except for the presence of calcium phosphate particles (Vitoss® micromorsels) were evident throughout as shown in FIG. 12. In addition, amorphous and ordered crystals appeared to be associated with both PCL and calcium phosphate.

Figure 13A:
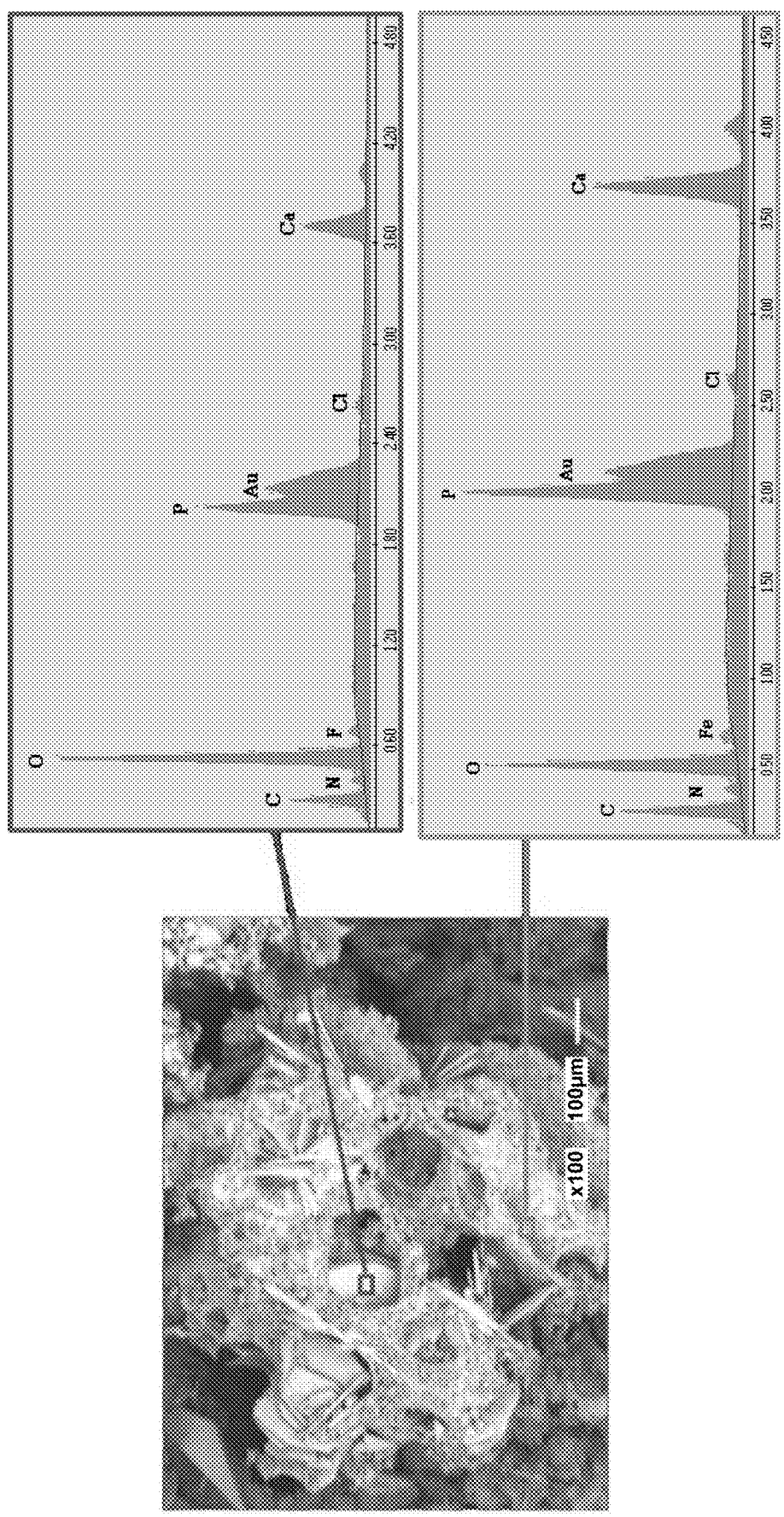
FIG. 13A depicts EDAX data from regions of a scaffold in accordance with some embodiments of the present invention.
Figure 13B:
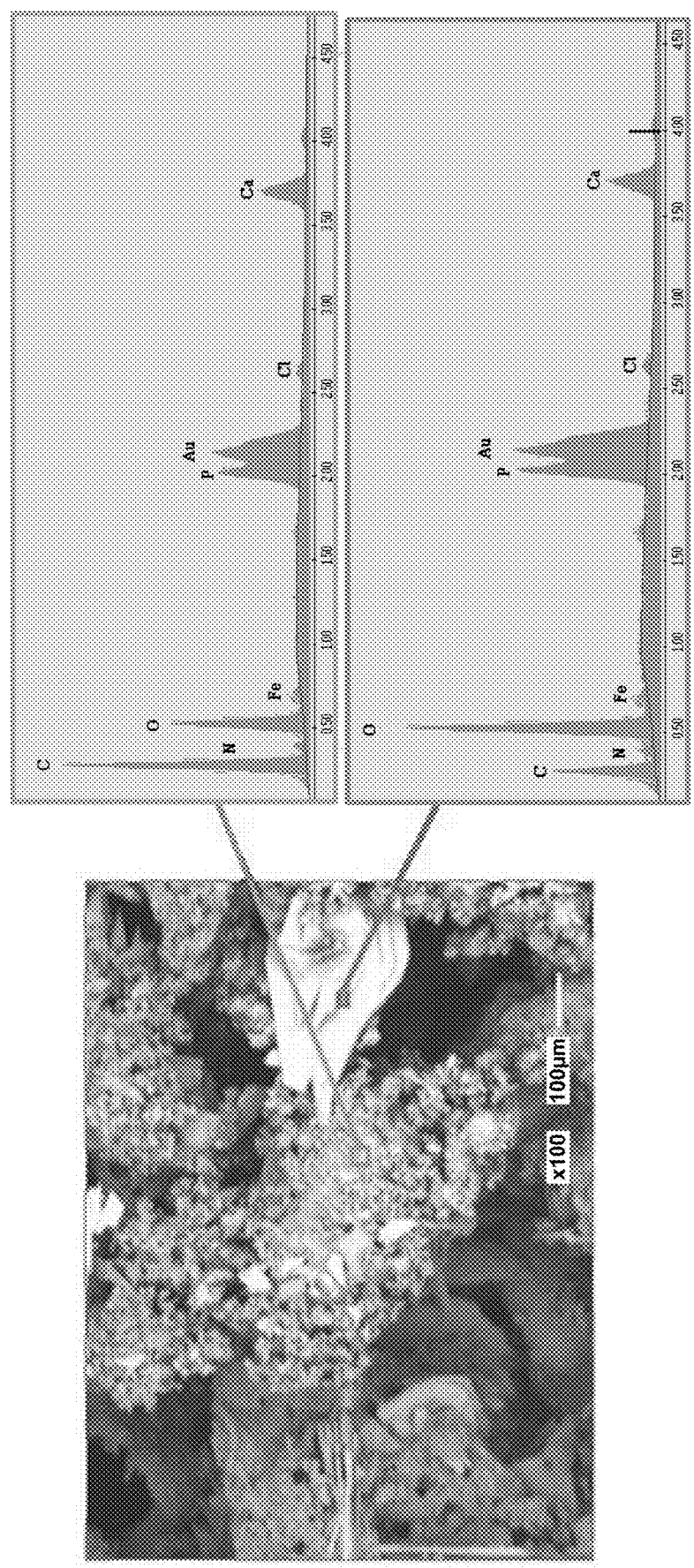
FIG. 13B depicts EDAX data from regions of the scaffold depicted in FIG. 12 in accordance with some embodiments of the present invention.

EDAX analysis (FIG. 13A, 13B) of regions of the scaffold depicted in FIG. 12 indicated the crystals comprised calcium phosphate. It is speculated that the crystals may arise from acid solubilization (in GAA) of at least part of the calcium phosphate and then recrystallization of the calcium phosphate on the PCL. Calcium phosphate crystal deposition on the surface of the scaffold may be minimized if desired. For example, after precipitation of PCL, a copious water rinse and/or base neutralization of GAA could be performed, optionally followed by rapid drying.

Experimental Example 6

Scaffold Thickness as a Function of Amount of Precipitating Agent

Experimental Example 6 studies scaffold dimensions and quality as a function of an amount of precipitating agent. Examples 6-1 through 6-5, the results of which are depicted in FIG. 14 were made using the same methods, except different amounts of precipitating agent were used in each Example. Comparative Example 6-1, the result of which is depicted in FIG. 14, was made using the same methods, except omitting a precipitating agent. Scaffolds in Experimental Example 6 did not include a calcium phosphate and/or bioactive additive, such as Vitoss® micromorsels.

Example 6-1

Scaffold Prepared from 10% PCL-GAA Solution Using 1 g Water

Figure 14A:
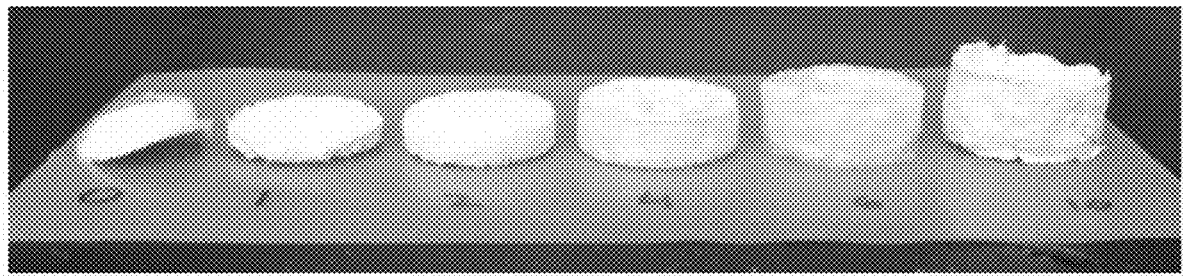
FIG. 14A depicts scaffolds formed using different amounts of precipitating agent in accordance with some embodiments of the present invention.

A 10% PCL-GAA solution was prepared by the same methods as described in Example 1-2. About 2 g of the 10% PCL-GAA solution were added to a 25 ml borosilicate glass beaker (Kimax®, available from Kimble). About 1 g of water was added dropwise to the surface of the 10% PCL-GAA solution. The water was added over a period of less than one minute. The mixture was allowed to incubate for about 15 to about 30 minutes at room temperature and ambient pressure conditions. After the incubation period the scaffold was dried at room temperature and atmospheric conditions for about 2 to 3 days and removed from the beaker. The scaffold is depicted in FIG. 14A and the thickness of the scaffold is depicted in comparison to Examples 6-2 through 6 and Comparative Example 6-1 in FIG. 14B.

Examples 6-2 Through 6-5

Scaffold Prepared from 10% PCL-GAA Solution Using 2 g, 4 g, 6 g, and 10 g Water

Examples 6-2 through 6-5 are made using the same procedure described for Example 6-1, except about 2 g, about 4 g, about 6 g, and about 10 g of water, respectively, were added dropwise to the 10 wt % PCL-GAA solution. The resulting scaffolds and thickness comparisons are depicted in FIG. 14.

Comparative Example 6-1

Scaffold Prepared from 10% PCL-GAA Solution and Air Drying

Figure 14B:
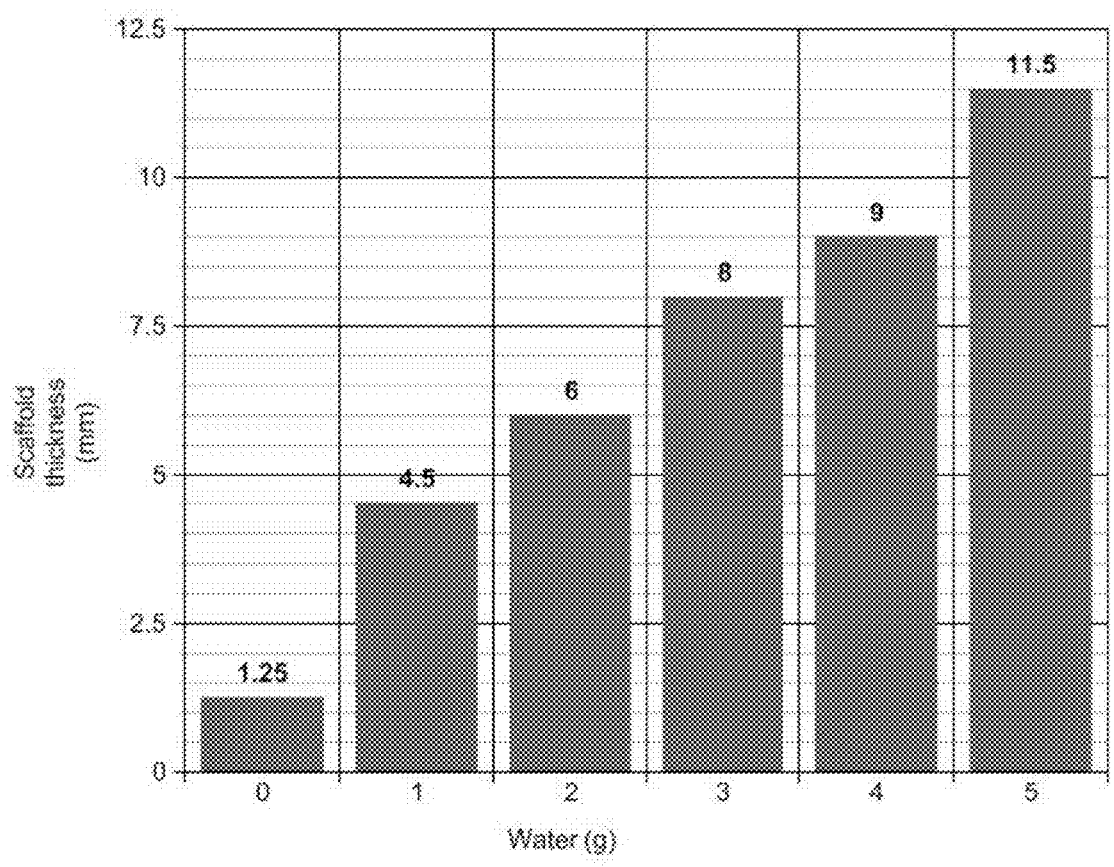
FIG. 14B depicts the thickness variation of the scaffolds depicted in FIG. 14A as function of the amount of precipitating agent added in accordance with some embodiments of the present invention.

Comparative Example 6-1 is made using the same procedure described for Example 6-1, except water was omitted. The resulting scaffold and thickness comparison to the other Examples is depicted in FIGS. 14A-14B.

As shown in FIG. 14A, the scaffolds of Examples 6-2 through 6-5 have a bright white, styrofoam-like appearance, and are porous. The scaffolds expand in height relative to the amount of water added up to about 6 g (Example 6-4). At higher amounts of water (8 g, not shown) or 10 g (Example 6-5) the scaffolds continue to expand to greater heights but their shapes become irregular. In contrast, Comparative Example 6-1, where water was not added, formed a thin, slightly flexible by manual manipulation, wrinkled disk with little or no apparent porosity.

Comparative Example 7

Scaffold Prepared Using a Different Order of Process Steps

Figure 15:
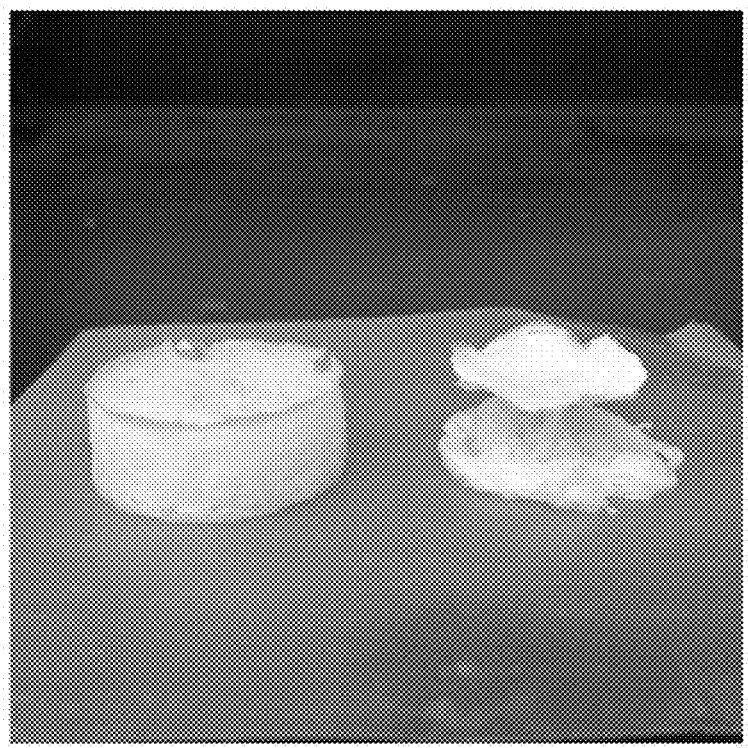
FIG. 15 depicts scaffolds formed using different orders of processing steps in accordance with some embodiments of the present invention.

Comparative Example 7 is made using the same procedure described for Example 6-4, except about 6 g of water was added to the borosilicate beaker, and 2 g of 10% PCL-GAA solution was added dropwise to the water. The resulting scaffold is depicted in FIG. 15 in comparison to the scaffold of Example 6-4. The scaffold of Comparative Example 6-2 is mushroom-shaped and has a non-homogenous density throughout the scaffold. The scaffold is also denser than that of Example 6-4.

Experimental Example 8

Scaffold Quality as a Function of Molecular Weight

Experimental Example 8 studies scaffold quality as a function of molecular weight of PCL. Examples 7-1 and Comparative Examples 8-1 and 8-2 were made using the same methods, except different molecular weights for each polymer.

Example 8-1

Scaffold Prepared from 10% PCL-GAA Solution Using Mn=80,000 g/Mol PCL

The scaffold of Example 7-1 was prepared by the same procedure as Example 1-2, except PCL pellets (Sigma-Aldrich Chemicals, Lot No. MKBV3325V) having Mn=80,000 g/mol were used in place of PCL filaments.

Comparative Example 8-1

Scaffold Prepared from 10% PCL-GAA Solution Using Mn=45,000 g/mol PCL

The scaffold of Comparative Example 7-1 was prepared by the same procedure as Example 1-2, except PCL pellets (Sigma-Aldrich Chemicals, Lot No. MKBT6624V) having Mn=45,000 g/mol were used in place of PCL filaments.

Comparative Example 8-2

Scaffold Prepared from 10% PCL-GAA Solution Using Mn=14,000 g/mol PCL

The scaffold of Comparative Example 7-2 was prepared by the same procedure as Example 1-2, except PCL pellets (Sigma-Aldrich Chemicals, Lot No. MKBR890V) having Mn=14,000 g/mol were used in place of PCL filaments.

Upon removing the scaffold of Example 7-1 from the mold, the scaffold was intact and robust. In contrast, the scaffold of Comparative Example 7-1 was partially intact and insufficiently robust. The scaffold of Comparative Example 7-2 was not robust and fell apart upon removal from the mold.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of forming a scaffold, comprising:
dissolving a polymer in a solvent to form a polymer solution, wherein an amount of polymer dissolved in the polymer solution ranges from about 4 wt % to about 15 wt %, relative to the total weight of the polymer solution;
adding at least one of calcium phosphate or a bioactive additive to the polymer solution to form a mixture;
adding a precipitating agent drop wise to the mixture;
precipitating and expanding the polymer from the mixture, by the addition of the precipitating agent, to form the scaffold; and
removing the solvent from the scaffold,
wherein the scaffold includes a polymer matrix made of the polymer, wherein the at least one of calcium phosphate or bioactive additive are embedded in the polymer matrix,
wherein the calcium phosphate has pore sizes ranging from 1 μm to 2000 μm,
wherein the bioactive additive has particle sizes ranging from 20 μm to 200 μm,
wherein the solvent is selected from the group consisting of glacial acetic acid (GAA), acetic acid, anisole, chloroform, methylene chloride, acetylchloride, 2,2,2-trifluoroethanol, trifluoroacetic acid, 1,2-dichloroethane, and mixtures thereof, and
wherein the time to form the scaffold by precipitation of the polymer ranges from about 1 minute to about 1 hour.

2. The method of claim 1, further comprising:
prior to adding the at least one of calcium phosphate or bioactive additive to the polymer solution, soaking the at least one of calcium phosphate or bioactive additive with the precipitating agent to form a precipitating agent-soaked additive; and
freezing the precipitating agent-soaked additive.

3. The method of claim 1, further comprising:
prior to precipitating the polymer, freezing the mixture.

4. The method of claim 1, wherein the precipitating agent is selected from the group consisting of water, ethanol, 1-propanol, isopropyl ether, 2-butanol, hexane, and mixtures thereof.

5. The method of claim 1, further comprising:
prior to precipitating the polymer, placing the mixture into a mold.

6. The method of claim 1, wherein the polymer is selected from the group consisting of polycaprolactones (PCL), polyglycolides (PGA), polylactic acids (PLA), polyethylene, polypropylene, polystyrene, poly(D,L-lactic-co-glycolide) (PLGA), polyglycolic acid (PGA), poly-L-Lactic acid (PL-LA), polysulfones, polyolefins, polyvinyl alcohol (PVA), polyalkenoics, polyacrylic acids (PAA), polyesters, lower alkyl cellulose ethers, methylcellulose, sodium carboxymethyl cellulose, hydroxyethyl cellulose, hydroxypropyl cellulose, hydroxypropylmethylcellulose, carboxymethyl cellulose, and mixtures thereof.

7. The method of claim 1, wherein the calcium phosphate is selected from the group consisting of tetra-calcium phosphate, di-calcium phosphate, dicalcium phosphate dihydrous, dicalcium phosphate anhydrous, tri-calcium phosphate, mono-calcium phosphate, β-tricalcium phosphate, α-tricalcium phosphate, oxyapatite, hydroxyapatite, and mixtures thereof.

8. The method of claim 1, wherein the calcium phosphate is porous.

9. The method of claim 1, wherein the bioactive additive is selected from the group consisting of bioactive glass, bone chips, demineralized bone chips or powder, living cells, lyophilized bone marrow, collagen, other bioactive proteins or growth factors, biologics, peptides, glycosaminoglycans, anti-inflammatory compounds, antibiotics, anti-microbial elements, and mixtures thereof.

10. The method of claim 1, wherein the polymer is polycaprolactone (PCL) and wherein the solvent is glacial acetic acid (GAA).

11. The method of claim 1, wherein the polymer is polycaprolactone (PCL) and wherein the solvent is anisole.

12. The method of claim 1, wherein the calcium phosphate is β-tricalcium phosphate (β-TCP).

13. The method of claim 1, wherein an amount of calcium phosphate ranges from about 20 wt % to about 30 wt %, relative to the total weight of the mixture.

14. The method of claim 1, wherein the polymer has a molecular weight ranging from about 3,000 g/mol to about 150,000 g/mol.

15. The method of claim 1, wherein a weight ratio of the precipitating agent to the polymer solution ranges from about 0.05:1 to about 3.5:1.

16. The method of claim 1, wherein a weight ratio of the precipitating agent to the polymer solution ranges from about 0.5:1 to 3:1.

17. The method of claim 1, wherein the time to form the scaffold by precipitation of the polymer ranges from about 5 minutes to about 30 minutes.

18. The method of claim 1, wherein the scaffold comprises an amorphous polymer matrix.

19. The method of claim 1, wherein the polymer is polycaprolactone (PCL), wherein the solvent is glacial acetic acid (GAA), wherein the precipitating agent is water,
wherein a weight ratio of the precipitating agent to the polymer solution ranges from about 0.05:1 to about 3.5:1.

20. The method of claim 1, wherein a weight ratio of the precipitating agent to the polymer solution ranges from about 0.5:1 to 3:1, and
wherein an amount of polymer dissolved in the polymer solution ranges from about 10 wt % to about 15 wt %, relative to the total weight of the polymer solution.

* * * * *